United States Patent
Jacobson

(10) Patent No.: US 10,238,883 B2
(45) Date of Patent: *Mar. 26, 2019

(54) LEADLESS CARDIAC PACEMAKER SYSTEM FOR USAGE IN COMBINATION WITH AN IMPLANTABLE CARDIOVERTER-DEFIBRILLATOR

(71) Applicant: Pacesetter, Inc., Santa Clara, CA (US)

(72) Inventor: Peter M. Jacobson, Livermore, CA (US)

(73) Assignee: Pacesetter Inc., Sunnyvale, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/845,043

(22) Filed: Dec. 18, 2017

(65) Prior Publication Data

US 2018/0126180 A1 May 10, 2018

Related U.S. Application Data

(60) Division of application No. 15/596,290, filed on May 16, 2017, now Pat. No. 9,872,999, which is a division
(Continued)

(51) Int. Cl.
*A61N 1/39* (2006.01)
*A61N 1/05* (2006.01)
(Continued)

(52) U.S. Cl.
CPC .......... *A61N 1/3962* (2013.01); *A61N 1/056* (2013.01); *A61N 1/059* (2013.01); *A61N 1/0573* (2013.01);
(Continued)

(58) Field of Classification Search
CPC .. A61N 1/3962; A61N 1/3621; A61N 1/3925; A61N 1/3704; A61N 1/3706;
(Continued)

(56) References Cited

U.S. PATENT DOCUMENTS 3,199,508 A 8/1965 Roth et al.
3,212,496 A 10/1965 Preston et al.
(Continued)

FOREIGN PATENT DOCUMENTS

EP 362611 A1 4/1990
EP 1115329 A2 7/2001
(Continued)

OTHER PUBLICATIONS

Notice of Allowance for U.S. Appl. No. 11/549,581, dated Apr. 25, 2016.
(Continued)

*Primary Examiner* — Rex R Holmes
(74) *Attorney, Agent, or Firm* — Theresa A. Raymer

(57) ABSTRACT

A cardiac pacing system comprising one or more leadless cardiac pacemakers configured for implantation in electrical contact with a cardiac chamber and configured to perform cardiac pacing functions in combination with a co-implanted implantable cardioverter-defibrillator (ICD). The leadless cardiac pacemaker comprises at least two leadless electrodes configured for delivering cardiac pacing pulses, sensing evoked and/or natural cardiac electrical signals, and bidirectionally communicating with the co-implanted ICD.

20 Claims, 14 Drawing Sheets

Related U.S. Application Data of application No. 15/208,194, filed on Jul. 12, 2016, now Pat. No. 9,687,666, which is a continuation of application No. 14/885,853, filed on Oct. 16, 2015, now Pat. No. 9,409,033, which is a division of application No. 14/318,201, filed on Jun. 27, 2014, now Pat. No. 9,192,774, which is a division of application No. 13/866,803, filed on Apr. 19, 2013, now Pat. No. 8,798,745, which is a division of application No. 11/549,599, filed on Oct. 13, 2006, now Pat. No. 8,457,742.

(60) Provisional application No. 60/761,531, filed on Jan. 24, 2006, provisional application No. 60/761,740, filed on Jan. 24, 2006, provisional application No. 60/749,017, filed on Dec. 10, 2005, provisional application No. 60/739,901, filed on Nov. 26, 2005, provisional application No. 60/737,296, filed on Nov. 16, 2005, provisional application No. 60/729,671, filed on Oct. 24, 2005, provisional application No. 60/726,706, filed on Oct. 14, 2005.

(51) Int. Cl.

| | | |
|---|---|---|
| *A61N 1/362* | (2006.01) | |
| *A61N 1/365* | (2006.01) | |
| *A61N 1/368* | (2006.01) | |
| *A61N 1/372* | (2006.01) | |
| *A61N 1/375* | (2006.01) | |
| *H04B 13/00* | (2006.01) | |
| *A61N 1/37* | (2006.01) | |
| *A61M 25/06* | (2006.01) | |

(52) U.S. Cl.
CPC ............ *A61N 1/0587* (2013.01); *A61N 1/368* (2013.01); *A61N 1/3621* (2013.01); *A61N 1/3627* (2013.01); *A61N 1/3684* (2013.01); *A61N 1/36514* (2013.01); *A61N 1/372* (2013.01); *A61N 1/3704* (2013.01); *A61N 1/375* (2013.01); *A61N 1/3706* (2013.01); *A61N 1/3708* (2013.01); *A61N 1/3727* (2013.01); *A61N 1/3756* (2013.01); *A61N 1/37205* (2013.01); *A61N 1/37217* (2013.01); *A61N 1/37288* (2013.01); *A61N 1/3925* (2013.01); *A61N 1/3956* (2013.01); *H04B 13/005* (2013.01); *A61M 25/0662* (2013.01); *A61N 1/36542* (2013.01); *A61N 1/37252* (2013.01); *A61N 2001/058* (2013.01)

(58) Field of Classification Search
CPC .. A61N 1/0587; A61N 1/3727; A61N 1/3956; A61N 1/372; A61N 1/056; A61N 1/368; A61N 1/3756; A61N 1/3627; A61N 1/03; H04B 13/005
See application file for complete search history.

(56) References Cited

U.S. PATENT DOCUMENTS

| | | |
|---|---|---|
| 3,218,638 A | 11/1965 | Honig et al. |
| 3,241,556 A | 3/1966 | Zacouto |
| 3,478,746 A | 11/1969 | Greatbatch |
| 3,603,881 A | 9/1971 | Thornton |
| 3,727,616 A | 4/1973 | Lenzkes |
| 3,757,778 A | 9/1973 | Graham |
| 3,823,708 A | 7/1974 | Lawhorn |
| 3,830,228 A | 8/1974 | Foner et al. |
| 3,835,864 A | 9/1974 | Rasor et al. |
| 3,836,798 A | 9/1974 | Greatbatch |
| 3,870,051 A | 3/1975 | Brindley |
| 3,872,251 A | 3/1975 | Auerbach et al. |
| 3,905,364 A | 9/1975 | Cudahy et al. |
| 3,940,692 A | 2/1976 | Neilson |
| 3,943,926 A | 3/1976 | Arvizu |
| 3,943,936 A | 3/1976 | Rasor et al. |
| 3,946,744 A | 3/1976 | Auerbach |
| 3,952,750 A | 4/1976 | Mirowski et al. |
| 4,027,663 A | 6/1977 | Fischler et al. |
| 4,072,154 A | 2/1978 | Anderson et al. |
| 4,083,366 A | 4/1978 | Gombrich et al. |
| 4,087,389 A | 5/1978 | Coppola et al. |
| 4,102,344 A | 7/1978 | Conway et al. |
| 4,146,029 A | 3/1979 | Ellinwood |
| 4,151,513 A | 4/1979 | Barthel et al. |
| 4,151,540 A | 4/1979 | Sander et al. |
| 4,152,540 A | 5/1979 | Duncan et al. |
| 4,173,221 A | 11/1979 | McLaughlin et al. |
| 4,187,854 A | 2/1980 | Citron et al. |
| 4,210,149 A | 7/1980 | Heilman et al. |
| RE30,366 E | 8/1980 | Rasnor et al. |
| 4,223,678 A | 9/1980 | Langer et al. |
| 4,250,888 A | 2/1981 | Grosskopf et al. |
| 4,256,115 A | 3/1981 | Bilitch et al. |
| 4,296,756 A | 10/1981 | Dunning et al. |
| 4,310,000 A | 1/1982 | Lindemans et al. |
| 4,312,354 A | 1/1982 | Walters et al. |
| 4,318,412 A | 3/1982 | Stanly et al. |
| 4,336,810 A | 6/1982 | Anderson et al. |
| 4,350,169 A | 9/1982 | Dutcher et al. |
| 4,374,382 A | 2/1983 | Markowitz |
| 4,406,288 A | 9/1983 | Horwinski et al. |
| 4,411,271 A | 10/1983 | Markowitz et al. |
| 4,418,695 A | 12/1983 | Buffet et al. |
| 4,424,551 A | 1/1984 | Stevenson et al. |
| 4,428,378 A | 1/1984 | Anderson et al. |
| 4,440,173 A | 4/1984 | Hudziak et al. |
| 4,442,840 A | 4/1984 | Wojciechowicz et al. |
| 4,453,162 A | 6/1984 | Money et al. |
| 4,458,692 A | 7/1984 | Simson et al. |
| 4,481,950 A | 11/1984 | Duggan et al. |
| 4,513,743 A | 4/1985 | Van et al. |
| 4,516,579 A | 5/1985 | Irnich et al. |
| 4,522,208 A | 6/1985 | Buffet et al. |
| 4,524,774 A | 6/1985 | Hildebrandt |
| 4,531,527 A | 7/1985 | Reinhold et al. |
| 4,543,955 A | 10/1985 | Schroeppel |
| 4,550,370 A | 10/1985 | Baker et al. |
| 4,552,127 A | 11/1985 | Schiff et al. |
| 4,552,154 A | 11/1985 | Hartlaub et al. |
| 4,562,846 A | 1/1986 | Cox et al. |
| 4,586,508 A | 5/1986 | Batina et al. |
| 4,606,352 A | 8/1986 | Geddes et al. |
| 4,607,639 A | 8/1986 | Tanagho et al. |
| 4,612,934 A | 9/1986 | Borkan |
| 4,625,730 A | 12/1986 | Fountain et al. |
| 4,679,144 A | 7/1987 | Cox et al. |
| 4,681,111 A | 7/1987 | Silvian |
| 4,681,117 A | 7/1987 | Brodman et al. |
| 4,702,253 A | 10/1987 | Nappholz et al. |
| 4,719,920 A | 1/1988 | Alt et al. |
| 4,722,342 A | 2/1988 | Amundson et al. |
| 4,750,495 A | 6/1988 | Moore et al. |
| 4,763,340 A | 8/1988 | Yoneda et al. |
| 4,763,655 A | 8/1988 | Wirtzfeld et al. |
| 4,787,389 A | 11/1988 | Tarjan et al. |
| 4,791,931 A | 12/1988 | Slate et al. |
| 4,793,353 A | 12/1988 | Borkan |
| 4,794,532 A | 12/1988 | Leckband et al. |
| 4,802,481 A | 2/1989 | Schroeppel et al. |
| 4,809,697 A | 3/1989 | Causey et al. |
| 4,827,940 A | 5/1989 | Mayer et al. |
| 4,830,006 A | 5/1989 | Haluska et al. |
| 4,844,076 A | 7/1989 | Lesho et al. |
| 4,846,195 A | 7/1989 | Alt et al. |
| 4,858,610 A | 8/1989 | Callaghan et al. |
| 4,860,750 A | 8/1989 | Frey et al. |
| 4,875,483 A | 10/1989 | Vollmann et al. |
| 4,880,004 A | 11/1989 | Baker et al. |
| 4,883,064 A | 11/1989 | Olson et al. |

(56) References Cited

U.S. PATENT DOCUMENTS

| | | |
|---|---|---|
| 4,886,064 A | 12/1989 | Strandberg |
| 4,896,068 A | 1/1990 | Nilsson et al. |
| 4,903,701 A | 2/1990 | Moore et al. |
| 4,905,708 A | 3/1990 | Davies |
| 4,926,863 A | 5/1990 | Alt |
| 4,974,589 A | 12/1990 | Sholder et al. |
| 4,987,897 A | 1/1991 | Funke |
| 4,995,390 A | 2/1991 | Cook et al. |
| 5,010,887 A | 4/1991 | Thornander |
| 5,012,806 A | 5/1991 | De Bellis et al. |
| 5,014,700 A | 5/1991 | Alt |
| 5,014,701 A | 5/1991 | Pless et al. |
| 5,031,615 A | 7/1991 | Alt |
| 5,040,533 A | 8/1991 | Fearnot et al. |
| 5,040,534 A | 8/1991 | Mann et al. |
| 5,040,536 A | 8/1991 | Riff |
| 5,042,497 A | 8/1991 | Shapland et al. |
| 5,052,399 A | 10/1991 | Olive et al. |
| 5,058,581 A | 10/1991 | Silvian |
| 5,065,759 A | 11/1991 | Begemann et al. |
| 5,076,270 A | 12/1991 | Stutz et al. |
| 5,076,272 A | 12/1991 | Ferek-Petric et al. |
| 5,085,224 A | 2/1992 | Galen et al. |
| 5,086,772 A | 2/1992 | Larnard et al. |
| 5,088,488 A | 2/1992 | Markowitz et al. |
| 5,095,903 A | 3/1992 | Debellis |
| 5,109,845 A | 5/1992 | Yuuchi et al. |
| 5,111,816 A | 5/1992 | Pless et al. |
| 5,113,859 A | 5/1992 | Funke |
| 5,113,869 A | 5/1992 | Nappholz et al. |
| 5,133,350 A | 7/1992 | Duffin et al. |
| 5,135,004 A | 8/1992 | Adams et al. |
| 5,170,784 A | 12/1992 | Ramon et al. |
| 5,170,802 A | 12/1992 | Mehra et al. |
| 5,179,947 A | 1/1993 | Meyerson et al. |
| 5,184,616 A | 2/1993 | Weiss et al. |
| 5,193,539 A | 3/1993 | Schulman et al. |
| 5,193,540 A | 3/1993 | Schulman et al. |
| 5,193,550 A | 3/1993 | Duffin et al. |
| 5,217,010 A | 6/1993 | Tsitlik et al. |
| 5,247,945 A | 9/1993 | Heinze et al. |
| 5,259,394 A | 11/1993 | Bens et al. |
| 5,260,621 A | 11/1993 | Little et al. |
| 5,267,150 A | 11/1993 | Wilkinson |
| 5,282,841 A | 2/1994 | Szyszkowski et al. |
| 5,284,136 A | 2/1994 | Hauck et al. |
| 5,291,902 A | 3/1994 | Carman |
| 5,300,093 A | 4/1994 | Koestner et al. |
| 5,304,206 A | 4/1994 | Baker et al. |
| 5,304,209 A | 4/1994 | Adams et al. |
| 5,313,953 A | 5/1994 | Yomtov et al. |
| 5,318,596 A | 6/1994 | Barreras et al. |
| 5,324,316 A | 6/1994 | Schulman et al. |
| 5,331,966 A | 7/1994 | Bennett et al. |
| 5,333,095 A | 7/1994 | Stevenson et al. |
| 5,336,244 A | 8/1994 | Weijand et al. |
| 5,342,401 A | 8/1994 | Spano et al. |
| 5,354,317 A | 10/1994 | Alt et al. |
| 5,358,514 A | 10/1994 | Schulman et al. |
| 5,373,852 A | 12/1994 | Harrison et al. |
| 5,383,912 A | 1/1995 | Cox et al. |
| 5,383,915 A | 1/1995 | Adams |
| 5,404,877 A | 4/1995 | Nolan et al. |
| 5,405,367 A | 4/1995 | Schulman et al. |
| 5,406,444 A | 4/1995 | Selfried et al. |
| 5,411,532 A | 5/1995 | Mortazavi et al. |
| 5,411,535 A | 5/1995 | Fujii et al. |
| 5,411,537 A | 5/1995 | Munshi et al. |
| 5,417,222 A | 5/1995 | Dempsey et al. |
| 5,419,337 A | 5/1995 | Dempsey et al. |
| 5,431,171 A | 7/1995 | Harrison et al. |
| 5,446,447 A | 8/1995 | Carney et al. |
| 5,456,261 A | 10/1995 | Luczyk et al. |
| 5,466,246 A | 11/1995 | Silvian |
| 5,469,857 A | 11/1995 | Laurent et al. |
| 5,480,415 A | 1/1996 | Cox et al. |
| 5,481,262 A | 1/1996 | Urbas et al. |
| 5,522,876 A | 6/1996 | Rusink et al. |
| 5,531,779 A | 7/1996 | Dahl et al. |
| 5,531,781 A | 7/1996 | Alferness et al. |
| 5,531,783 A | 7/1996 | Giele et al. |
| 5,539,775 A | 7/1996 | Tuttle et al. |
| 5,549,654 A | 8/1996 | Powell et al. |
| 5,549,659 A | 8/1996 | Johansen et al. |
| 5,551,427 A | 9/1996 | Altman |
| 5,556,421 A | 9/1996 | Prutchi et al. |
| 5,562,717 A | 10/1996 | Tippey et al. |
| 5,571,143 A | 11/1996 | Hoegnelid et al. |
| 5,571,148 A | 11/1996 | Loeb et al. |
| 5,579,775 A | 12/1996 | Dempsey et al. |
| 5,586,556 A | 12/1996 | Spivey et al. |
| 5,591,217 A | 1/1997 | Barreras et al. |
| 5,598,848 A | 2/1997 | Swanson et al. |
| 5,649,952 A | 7/1997 | Lam et al. |
| 5,650,759 A | 7/1997 | Hittman et al. |
| 5,654,984 A | 8/1997 | Hershbarger et al. |
| 5,662,689 A | 9/1997 | Elsberry et al. |
| 5,669,391 A | 9/1997 | Williams |
| 5,674,259 A | 10/1997 | Gray |
| 5,676,153 A | 10/1997 | Smith et al. |
| 5,693,076 A | 12/1997 | Kaemmerer et al. |
| 5,694,940 A | 12/1997 | Unger et al. |
| 5,694,952 A | 12/1997 | Lidman et al. |
| 5,697,958 A | 12/1997 | Paul et al. |
| 5,702,427 A | 12/1997 | Ecker et al. |
| 5,725,559 A | 3/1998 | Alt et al. |
| 5,728,154 A | 3/1998 | Crossett et al. |
| 5,730,143 A | 3/1998 | Schwarzberg |
| 5,735,880 A | 4/1998 | Prutchi et al. |
| 5,738,102 A | 4/1998 | Lemelson |
| 5,740,811 A | 4/1998 | Hedberg et al. |
| 5,741,314 A | 4/1998 | Daly et al. |
| 5,766,231 A | 6/1998 | Erickson et al. |
| 5,792,202 A | 8/1998 | Rueter et al. |
| 5,792,205 A | 8/1998 | Alt et al. |
| 5,792,208 A | 8/1998 | Gray |
| 5,810,735 A | 9/1998 | Halperin et al. |
| 5,814,076 A | 9/1998 | Brownlee |
| 5,814,087 A | 9/1998 | Renirie et al. |
| 5,814,089 A | 9/1998 | Stokes et al. |
| 5,824,016 A | 10/1998 | Ekwall et al. |
| 5,871,451 A | 2/1999 | Unger et al. |
| 5,876,353 A | 3/1999 | Riff |
| 5,876,425 A | 3/1999 | Gord et al. |
| 5,891,178 A | 4/1999 | Mann et al. |
| 5,899,928 A | 5/1999 | Sholder et al. |
| 5,935,079 A | 8/1999 | Swanson et al. |
| 5,954,761 A | 9/1999 | Machek et al. |
| 5,957,861 A | 9/1999 | Combs et al. |
| 5,984,861 A | 11/1999 | Crowley |
| 5,987,352 A | 11/1999 | Klein et al. |
| 5,995,876 A | 11/1999 | Kruse et al. |
| 5,999,857 A | 12/1999 | Weijand et al. |
| 6,002,969 A | 12/1999 | Machek et al. |
| 6,004,269 A | 12/1999 | Crowley et al. |
| 6,061,596 A | 5/2000 | Richmond et al. |
| 6,076,016 A | 6/2000 | Feierbach |
| 6,080,187 A | 6/2000 | Alt et al. |
| 6,093,146 A | 7/2000 | Filangeri |
| 6,096,065 A | 8/2000 | Crowley |
| 6,102,874 A | 8/2000 | Stone et al. |
| 6,112,116 A | 8/2000 | Fischell et al. |
| 6,115,628 A | 9/2000 | Stadler et al. |
| 6,115,630 A | 9/2000 | Stadler et al. |
| 6,115,636 A | 9/2000 | Ryan |
| 6,119,031 A | 9/2000 | Crowley et al. |
| 6,125,290 A | 9/2000 | Miesel et al. |
| 6,125,291 A | 9/2000 | Miesel et al. |
| 6,128,526 A | 10/2000 | Stadler et al. |
| 6,129,751 A | 10/2000 | Lucchesi et al. |
| 6,132,390 A | 10/2000 | Cookston et al. |
| 6,132,456 A | 10/2000 | Sommer et al. |
| 6,134,459 A | 10/2000 | Roberts et al. |
| 6,134,470 A | 10/2000 | Hartlaub |

(56) References Cited

U.S. PATENT DOCUMENTS

| | | |
|---|---|---|
| 6,139,510 A | 10/2000 | Palermo |
| 6,141,584 A | 10/2000 | Rockwell et al. |
| 6,141,588 A | 10/2000 | Cox et al. |
| 6,141,592 A | 10/2000 | Pauly et al. |
| 6,144,866 A | 11/2000 | Miesel et al. |
| 6,148,230 A | 11/2000 | Kenknight et al. |
| 6,152,882 A | 11/2000 | Prutchi et al. |
| 6,163,723 A | 12/2000 | Roberts et al. |
| 6,164,284 A | 12/2000 | Schulman et al. |
| 6,167,310 A | 12/2000 | Grevious et al. |
| 6,178,349 B1 | 1/2001 | Kieval et al. |
| 6,178,356 B1 | 1/2001 | Chastain et al. |
| 6,185,443 B1 | 2/2001 | Crowley |
| 6,185,452 B1 | 2/2001 | Schulman et al. |
| 6,185,464 B1 | 2/2001 | Bonner et al. |
| 6,188,932 B1 | 2/2001 | Lindegren et al. |
| 6,190,324 B1 | 2/2001 | Kieval et al. |
| 6,198,952 B1 | 3/2001 | Miesel et al. |
| 6,201,993 B1 | 3/2001 | Kruse et al. |
| 6,208,894 B1 | 3/2001 | Schulman et al. |
| 6,208,900 B1 | 3/2001 | Ecker et al. |
| 6,223,081 B1 | 4/2001 | Kerver et al. |
| 6,230,059 B1 | 5/2001 | Duffin et al. |
| 6,236,882 B1 | 5/2001 | Lee et al. |
| 6,240,321 B1 | 5/2001 | Janke et al. |
| 6,243,608 B1 | 6/2001 | Pauly et al. |
| 6,248,080 B1 | 6/2001 | Miesel et al. |
| 6,263,245 B1 | 7/2001 | Snell |
| 6,265,100 B1 | 7/2001 | Saaski et al. |
| 6,266,554 B1 | 7/2001 | Hsu et al. |
| 6,266,564 B1 | 7/2001 | Hill et al. |
| 6,272,379 B1 | 8/2001 | Fischell et al. |
| 6,280,409 B1 | 8/2001 | Stone et al. |
| 6,289,229 B1 | 9/2001 | Crowley et al. |
| 6,306,088 B1 | 10/2001 | Krausman et al. |
| 6,310,960 B1 | 10/2001 | Saaski et al. |
| 6,315,721 B2 | 11/2001 | Schulman et al. |
| 6,324,418 B1 | 11/2001 | Crowley et al. |
| 6,324,421 B1 | 11/2001 | Stadler et al. |
| RE37,463 E | 12/2001 | Altman et al. |
| 6,343,227 B1 | 1/2002 | Crowley et al. |
| 6,343,233 B1 | 1/2002 | Werner et al. |
| 6,347,245 B1 | 2/2002 | Lee et al. |
| 6,358,202 B1 | 3/2002 | Arent et al. |
| 6,361,522 B1 | 3/2002 | Scheiner et al. |
| 6,363,282 B1 | 3/2002 | Nichols et al. |
| 6,364,831 B1 | 4/2002 | Crowley et al. |
| 6,370,434 B1 | 4/2002 | Zhang et al. |
| 6,381,492 B1 | 4/2002 | Rockwell et al. |
| 6,381,493 B1 | 4/2002 | Stadler et al. |
| 6,381,494 B1 | 4/2002 | Gilkerson et al. |
| 6,383,209 B1 | 5/2002 | Crowley et al. |
| 6,385,593 B2 | 5/2002 | Linberg et al. |
| 6,386,882 B1 | 5/2002 | Linberg et al. |
| 6,397,100 B2 | 5/2002 | Stadler et al. |
| 6,402,689 B1 | 6/2002 | Scarantino et al. |
| 6,405,073 B1 | 6/2002 | Crowley et al. |
| 6,405,083 B1 | 6/2002 | Rockwell et al. |
| 6,409,674 B1 | 6/2002 | Brockway et al. |
| 6,409,675 B1 | 6/2002 | Turcott et al. |
| 6,412,490 B1 | 7/2002 | Lee et al. |
| 6,418,346 B1 | 7/2002 | Nelson et al. |
| 6,423,056 B1 | 7/2002 | Ishikawa et al. |
| 6,424,866 B2 | 7/2002 | Mika et al. |
| 6,428,484 B1 | 8/2002 | Battmer et al. |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,442,433 B1 | 8/2002 | Linberg et al. |
| 6,444,970 B1 | 9/2002 | Barbato et al. |
| 6,445,953 B1 | 9/2002 | Bulkes et al. |
| 6,458,145 B1 | 10/2002 | Ravenscroft et al. |
| 6,459,928 B2 | 10/2002 | Mika et al. |
| 6,459,937 B1 | 10/2002 | Morgan et al. |
| 6,466,820 B1 | 10/2002 | Juran et al. |
| 6,468,263 B1 | 10/2002 | Fischell et al. |
| 6,470,215 B1 | 10/2002 | Kraus et al. |
| 6,471,645 B1 | 10/2002 | Warkentin et al. |
| 6,472,991 B1 | 10/2002 | Schulman et al. |
| 6,477,424 B1 | 11/2002 | Thompson et al. |
| 6,480,733 B1 | 11/2002 | Turcott et al. |
| 6,482,154 B1 | 11/2002 | Haubrich et al. |
| 6,484,055 B1 | 11/2002 | Marcovecchio et al. |
| 6,484,057 B2 | 11/2002 | Ideker et al. |
| 6,490,487 B1 | 12/2002 | Kraus et al. |
| 6,496,715 B1 | 12/2002 | Lee et al. |
| 6,498,951 B1 | 12/2002 | Larson et al. |
| 6,500,168 B1 | 12/2002 | Jellie et al. |
| 6,501,983 B1 | 12/2002 | Natarajan et al. |
| 6,512,949 B1 | 1/2003 | Combs et al. |
| 6,512,959 B1 | 1/2003 | Gomperz et al. |
| 6,522,926 B1 | 2/2003 | Kieval et al. |
| 6,522,928 B2 | 2/2003 | Whitehurst et al. |
| 6,539,257 B1 | 3/2003 | Kenknight et al. |
| 6,542,781 B1 | 4/2003 | Koblish et al. |
| 6,556,860 B1 | 4/2003 | Groenewegen et al. |
| 6,558,321 B1 | 5/2003 | Burd et al. |
| 6,564,807 B1 | 5/2003 | Schulman et al. |
| 6,567,680 B2 | 5/2003 | Swetlik et al. |
| 6,571,120 B2 | 5/2003 | Hutten et al. |
| 6,574,509 B1 | 6/2003 | Kraus et al. |
| 6,574,511 B2 | 6/2003 | Lee et al. |
| 6,580,946 B2 | 6/2003 | Struble et al. |
| 6,580,948 B2 | 6/2003 | Haupert et al. |
| 6,584,351 B1 | 6/2003 | Ekwall et al. |
| 6,584,352 B2 | 6/2003 | Combs et al. |
| 6,589,187 B1 | 7/2003 | Dirnberger et al. |
| 6,592,518 B2 | 7/2003 | Denker et al. |
| 6,594,523 B1 | 7/2003 | Levine et al. |
| 6,597,948 B1 | 7/2003 | Rockwell et al. |
| 6,597,952 B1 | 7/2003 | Mika et al. |
| 6,609,023 B1 | 8/2003 | Fischell et al. |
| 6,611,710 B2 | 8/2003 | Gomperz et al. |
| 6,615,075 B2 | 9/2003 | Mlynash et al. |
| 6,622,043 B1 | 9/2003 | Kraus et al. |
| 6,647,292 B1 | 11/2003 | Bardy et al. |
| 6,648,823 B2 | 11/2003 | Thompson et al. |
| 6,649,078 B2 | 11/2003 | Yu et al. |
| 6,654,638 B1 | 11/2003 | Sweeney et al. |
| 6,658,285 B2 | 12/2003 | Potse et al. |
| 6,658,297 B2 | 12/2003 | Loeb et al. |
| 6,658,301 B2 | 12/2003 | Loeb et al. |
| 6,659,959 B2 | 12/2003 | Brockway et al. |
| 6,669,631 B2 | 12/2003 | Norris et al. |
| 6,681,135 B1 | 1/2004 | Davis et al. |
| 6,684,100 B1 | 1/2004 | Sweeney et al. |
| 6,687,540 B2 | 2/2004 | Marcovecchio et al. |
| 6,687,546 B2 | 2/2004 | Dennard et al. |
| 6,689,117 B2 | 2/2004 | Sweeney et al. |
| 6,690,959 B2 | 2/2004 | Thompson et al. |
| 6,694,191 B2 | 2/2004 | Starkweather et al. |
| 6,695,885 B2 | 2/2004 | Schulman et al. |
| 6,697,672 B2 | 2/2004 | Andersson et al. |
| 6,697,677 B2 | 2/2004 | Dahl et al. |
| 6,699,200 B2 | 3/2004 | Cao et al. |
| 6,702,857 B2 | 3/2004 | Shults et al. |
| 6,704,602 B2 | 3/2004 | Berg et al. |
| 6,711,440 B2 | 3/2004 | Deal et al. |
| 6,716,238 B2 | 4/2004 | Elliott et al. |
| 6,721,597 B1 | 4/2004 | Bardy et al. |
| 6,728,572 B2 | 4/2004 | Hsu et al. |
| 6,728,574 B2 | 4/2004 | Ujhelyi et al. |
| 6,728,576 B2 | 4/2004 | Thompson et al. |
| 6,731,976 B2 | 5/2004 | Penn et al. |
| 6,731,979 B2 | 5/2004 | MacDonald et al. |
| 6,733,485 B1 | 5/2004 | Whitehurst et al. |
| 6,735,474 B1 | 5/2004 | Loeb et al. |
| 6,735,475 B1 | 5/2004 | Whitehurst et al. |
| 6,738,670 B1 | 5/2004 | Almendinger et al. |
| 6,741,877 B1 | 5/2004 | Shults et al. |
| 6,741,886 B2 | 5/2004 | Yonce et al. |
| 6,746,404 B2 | 6/2004 | Schwartz et al. |
| 6,754,538 B2 | 6/2004 | Linberg et al. |
| 6,760,620 B2 | 7/2004 | Sippens et al. |

(56) References Cited

U.S. PATENT DOCUMENTS

| | | |
|---|---|---|
| 6,764,446 B2 | 7/2004 | Wolinsky et al. |
| 6,768,923 B2 | 7/2004 | Ding et al. |
| 6,783,499 B2 | 8/2004 | Schwartz et al. |
| 6,785,576 B2 | 8/2004 | Verness et al. |
| 6,786,860 B2 | 9/2004 | Maltan et al. |
| 6,792,314 B2 | 9/2004 | Byers et al. |
| 6,799,069 B2 | 9/2004 | Weiner et al. |
| 6,804,559 B1 | 10/2004 | Kraus et al. |
| 6,804,561 B2 | 10/2004 | Stover et al. |
| 6,809,507 B2 | 10/2004 | Morgan et al. |
| 6,811,533 B2 | 11/2004 | Dennard et al. |
| 6,813,519 B2 | 11/2004 | Bowman et al. |
| 6,821,154 B1 | 11/2004 | Canfield et al. |
| 6,823,217 B2 | 11/2004 | Rutten et al. |
| 6,824,512 B2 | 11/2004 | Warkentin et al. |
| 6,829,508 B2 | 12/2004 | Schulman et al. |
| 6,839,596 B2 | 1/2005 | Nelson et al. |
| 6,848,052 B2 | 1/2005 | Hamid et al. |
| 6,850,801 B2 | 2/2005 | Kieval et al. |
| 6,856,835 B2 | 2/2005 | Bardy et al. |
| 6,862,465 B2 | 3/2005 | Shults et al. |
| 6,862,480 B2 | 3/2005 | Cohen et al. |
| 6,865,420 B1 | 3/2005 | Kroll et al. |
| 6,869,404 B2 | 3/2005 | Schulhauser et al. |
| 6,871,099 B1 | 3/2005 | Whitehurst et al. |
| 6,878,112 B2 | 4/2005 | Linberg et al. |
| 6,879,695 B2 | 4/2005 | Maltan et al. |
| 6,879,855 B2 | 4/2005 | Schulman et al. |
| 6,882,875 B1 | 4/2005 | Crowley et al. |
| 6,889,081 B2 | 5/2005 | Hsu et al. |
| 6,893,395 B1 | 5/2005 | Kraus et al. |
| 6,895,279 B2 | 5/2005 | Loeb et al. |
| 6,895,281 B1 | 5/2005 | Amundson et al. |
| 6,896,651 B2 | 5/2005 | Gross et al. |
| 6,897,788 B2 | 5/2005 | Khair et al. |
| 6,901,294 B1 | 5/2005 | Whitehurst et al. |
| 6,901,296 B1 | 5/2005 | Whitehurst et al. |
| 6,907,285 B2 | 6/2005 | Denker et al. |
| 6,907,293 B2 | 6/2005 | Creasey et al. |
| 6,912,420 B2 | 6/2005 | Scheiner et al. |
| 6,917,833 B2 | 7/2005 | Denker et al. |
| 6,925,328 B2 | 8/2005 | Foster et al. |
| 6,931,327 B2 | 8/2005 | Goode et al. |
| 6,999,821 B2 | 2/2006 | Jenney et al. |
| 7,001,372 B2 | 2/2006 | Richter et al. |
| 7,023,359 B2 | 4/2006 | Goetz et al. |
| 7,027,876 B2 | 4/2006 | Casavant et al. |
| 7,146,222 B2 | 12/2006 | Boling et al. |
| 7,146,225 B2 | 12/2006 | Guenst et al. |
| 7,164,950 B2 | 1/2007 | Kroll et al. |
| 7,181,505 B2 | 2/2007 | Haller et al. |
| 7,187,971 B2 | 3/2007 | Sommer et al. |
| 7,200,437 B1 | 4/2007 | Nabutovsky et al. |
| 7,212,870 B1 | 5/2007 | Helland et al. |
| 7,277,754 B2 | 10/2007 | McCabe et al. |
| 7,289,853 B1 | 10/2007 | Campbell et al. |
| 7,307,544 B2 | 12/2007 | Kim et al. |
| 7,363,090 B2 | 4/2008 | Stevenson et al. |
| 7,532,933 B2 | 5/2009 | Lafontaine et al. |
| 7,558,631 B2 | 7/2009 | Cowan et al. |
| 7,565,195 B1 * | 7/2009 | Kroll ............... A61N 1/37288 607/2 |
| 7,616,991 B2 | 11/2009 | Mann et al. |
| 7,630,767 B1 | 12/2009 | Poore et al. |
| 7,634,313 B1 | 12/2009 | Kroll et al. |
| 7,650,186 B2 | 1/2010 | Hastings et al. |
| 7,848,823 B2 | 12/2010 | Drasler et al. |
| 7,937,148 B2 | 5/2011 | Jacobson et al. |
| 7,945,333 B2 | 5/2011 | Jacobson et al. |
| 7,991,467 B2 | 8/2011 | Markowitz |
| 8,010,209 B2 | 8/2011 | Jacobson et al. |
| 8,295,939 B2 | 10/2012 | Jacobson et al. |
| 8,352,025 B2 | 1/2013 | Jacobson et al. |
| 8,457,742 B2 | 6/2013 | Jacobson et al. |
| 8,788,053 B2 | 7/2014 | Jacobson et al. |
| 2001/0031999 A1 | 10/2001 | Carter et al. |
| 2002/0032467 A1 | 3/2002 | Shemer et al. |
| 2002/0077686 A1 | 6/2002 | Westlund et al. |
| 2002/0099423 A1 | 7/2002 | Berg et al. |
| 2002/0099430 A1 | 7/2002 | Verness et al. |
| 2002/0111662 A1 | 8/2002 | Iaizzo et al. |
| 2002/0116028 A1 | 8/2002 | Greatbatch et al. |
| 2002/0147488 A1 | 10/2002 | Doan et al. |
| 2003/0040666 A1 | 2/2003 | Rutten et al. |
| 2003/0141995 A1 | 7/2003 | Lin et al. |
| 2003/0158584 A1 | 8/2003 | Cates et al. |
| 2003/0163184 A1 | 8/2003 | Scheiner et al. |
| 2003/0199941 A1 | 10/2003 | Nielsen et al. |
| 2004/0011366 A1 | 1/2004 | Schulman et al. |
| 2004/0059392 A1 | 3/2004 | Parramon et al. |
| 2004/0116939 A1 | 6/2004 | Goode et al. |
| 2004/0133242 A1 | 7/2004 | Chapman et al. |
| 2004/0143262 A1 | 7/2004 | Visram et al. |
| 2004/0147973 A1 | 7/2004 | Hauser et al. |
| 2004/0167587 A1 | 8/2004 | Thompson et al. |
| 2004/0172116 A1 | 9/2004 | Seifert et al. |
| 2004/0193223 A1 | 9/2004 | Kramer et al. |
| 2004/0249417 A1 | 12/2004 | Ransbury et al. |
| 2004/0260349 A1 | 12/2004 | Stroebel et al. |
| 2005/0038474 A1 | 2/2005 | Wool et al. |
| 2005/0038491 A1 | 2/2005 | Haack et al. |
| 2005/0043765 A1 | 2/2005 | Williams et al. |
| 2005/0075682 A1 | 4/2005 | Schulman et al. |
| 2005/0096702 A1 | 5/2005 | Denker et al. |
| 2005/0131478 A1 | 6/2005 | Kim et al. |
| 2005/0149138 A1 | 7/2005 | Min et al. |
| 2005/0165465 A1 | 7/2005 | Pianca et al. |
| 2005/0267555 A1 | 12/2005 | Marnfeldt et al. |
| 2005/0288722 A1 | 12/2005 | Eigler et al. |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0105613 A1 | 5/2006 | Carroll et al. |
| 2006/0108335 A1 | 5/2006 | Zhao et al. |
| 2006/0121475 A1 | 6/2006 | Davids et al. |
| 2006/0135999 A1 | 6/2006 | Bodner et al. |
| 2006/0136004 A1 | 6/2006 | Cowan et al. |
| 2006/0161222 A1 | 7/2006 | Haubrich et al. |
| 2006/0241705 A1 | 10/2006 | Neumann et al. |
| 2006/0247750 A1 | 11/2006 | Seifert et al. |
| 2006/0282150 A1 | 12/2006 | Olson et al. |
| 2007/0016263 A1 | 1/2007 | Armstrong et al. |
| 2007/0043414 A1 | 2/2007 | Fifer et al. |
| 2007/0055184 A1 | 3/2007 | Echt et al. |
| 2007/0088394 A1 | 4/2007 | Jacobson et al. |
| 2007/0088396 A1 | 4/2007 | Jacobson et al. |
| 2007/0088397 A1 | 4/2007 | Jacobson et al. |
| 2007/0088398 A1 | 4/2007 | Jacobson et al. |
| 2007/0088400 A1 | 4/2007 | Jacobson et al. |
| 2007/0088405 A1 | 4/2007 | Jacobson et al. |
| 2007/0088418 A1 | 4/2007 | Jacobson et al. |
| 2007/0123923 A1 | 5/2007 | Lindstrom et al. |
| 2007/0142709 A1 | 6/2007 | Martone et al. |
| 2007/0167994 A1 | 7/2007 | Shelton et al. |
| 2007/0179552 A1 | 8/2007 | Dennis et al. |
| 2007/0270675 A1 | 11/2007 | Kane et al. |
| 2007/0276004 A1 | 11/2007 | Hirsch et al. |
| 2007/0276444 A1 | 11/2007 | Gelbart et al. |
| 2007/0293904 A1 | 12/2007 | Gelbart et al. |
| 2008/0004535 A1 | 1/2008 | Smits et al. |
| 2008/0021532 A1 | 1/2008 | Kveen et al. |
| 2008/0039738 A1 | 2/2008 | Dinsmoor et al. |
| 2008/0086168 A1 | 4/2008 | Cahill et al. |
| 2008/0091255 A1 | 4/2008 | Caparso et al. |
| 2008/0119911 A1 | 5/2008 | Rosero et al. |
| 2008/0243218 A1 | 10/2008 | Bottomley et al. |
| 2008/0269591 A1 | 10/2008 | Halperin et al. |
| 2008/0306359 A1 | 12/2008 | Zdeblick et al. |
| 2009/0018599 A1 | 1/2009 | Hastings et al. |
| 2009/0082827 A1 | 3/2009 | Kveen et al. |
| 2009/0082828 A1 | 3/2009 | Ostroff et al. |
| 2009/0149902 A1 | 6/2009 | Kumar et al. |
| 2009/0171408 A1 | 7/2009 | Solem et al. |

(56) References Cited

U.S. PATENT DOCUMENTS

| | | |
|---|---|---|
| 2010/0069983 A1 | 3/2010 | Peacock et al. |
| 2010/0198288 A1 | 8/2010 | Ostroff et al. |
| 2010/0249828 A1 | 9/2010 | Mavani et al. |
| 2010/0292541 A1 | 11/2010 | Hashiba et al. |
| 2010/0305653 A1 | 12/2010 | Lund et al. |
| 2010/0305656 A1 | 12/2010 | Imran et al. |
| 2010/0312332 A1 | 12/2010 | Forster et al. |
| 2011/0004117 A1 | 1/2011 | Neville et al. |
| 2011/0071586 A1 | 3/2011 | Jacobson et al. |
| 2011/0077708 A1 | 3/2011 | Ostroff et al. |
| 2011/0184492 A1 | 7/2011 | Martens et al. |
| 2011/0208260 A1 | 8/2011 | Jacobson et al. |
| 2011/0218587 A1 | 9/2011 | Jacobson et al. |
| 2011/0282423 A1 | 11/2011 | Jacobson et al. |
| 2012/0089198 A1 | 4/2012 | Ostroff et al. |
| 2012/0095539 A1 | 4/2012 | Khairkhahan et al. |
| 2012/0109236 A1 | 5/2012 | Jacobson et al. |
| 2012/0116489 A1 | 5/2012 | Khairkhahan et al. |
| 2012/0158111 A1 | 6/2012 | Khairkhahan et al. |
| 2012/0165827 A1 | 6/2012 | Khairkhahan et al. |
| 2012/0197373 A1 | 8/2012 | Khairkhahan et al. |
| 2013/0041422 A1 | 2/2013 | Jacobson et al. |
| 2013/0103109 A1 | 4/2013 | Jacobson et al. |
| 2013/0123875 A1 | 5/2013 | Varady et al. |
| 2014/0051965 A1 | 2/2014 | Zdeblick et al. |

FOREIGN PATENT DOCUMENTS

| | | |
|---|---|---|
| EP | 1741465 A1 | 1/2007 |
| JP | H04506167 | 10/1992 |
| JP | H05245215 | 9/1993 |
| JP | 2006507096 A | 3/2006 |
| JP | 2006516449 A | 7/2006 |
| JP | 2006526483 A | 11/2006 |
| WO | 9312714 A1 | 7/1993 |
| WO | 9837926 A1 | 9/1998 |
| WO | 0234333 A4 | 9/2002 |
| WO | 2004012811 A1 | 2/2004 |
| WO | 2006065394 A1 | 6/2006 |
| WO | 2007047681 A4 | 4/2007 |
| WO | 2007059386 A2 | 5/2007 |
| WO | 2008058265 A2 | 5/2008 |

OTHER PUBLICATIONS

Patent Board Decision for U.S. Appl. No. 11/549,581, dated Jan. 21, 2016.
Notice of Allowance for U.S. Appl. No. 14/885,853, dated Apr. 15, 2016.
Non-Final Office Action for U.S. Appl. No. 14/885,853, dated Nov. 18, 2015.
Notice of Allowance for U.S. Appl. No. 14/318,201, dated Sep. 23, 2015.
Terminal Disclaimer for U.S. Appl. No. 14/318,201, filed Sep. 16, 2015.
Non-Final Office Action for U.S. Appl. No. 14/318,201, dated Dec. 2, 2014.
Notice of Allowance for U.S. Appl. No. 12/953,282, dated Nov. 23, 2015.
Patent Board Decision for U.S. Appl. No. 12/953,282, dated May 27, 2015.
Non-Final Office Action for U.S. Appl. No. 12/953,282, dated Sep. 27, 2011.
Notice of Allowance for U.S. Appl. No. 13/098,266, dated May 22, 2015.
Final Office Action for U.S. Appl. No. 13/098,266, dated Jan. 29, 2015.
Non-Final Office Action for U.S. Appl. No. 13/098,266, dated Aug. 22, 2014.
Final Office Action for U.S. Appl. No. 13/098,266, dated Feb. 27, 2014.
Non-Final Office Action for U.S. Appl. No. 13/098,266, dated Oct. 10, 2013.
Non-Final Office Action for U.S. Appl. No. 13/098,266, dated May 31, 2013.
Final Office Action for U.S. Appl. No. 13/098,266, dated Jun. 22, 2012.
Non-Final Office Action for U.S. Appl. No. 13/098,266, dated Nov. 25, 2011.
Non-Final Office Action for U.S. Appl. No. 14/318,201, dated Apr. 30, 2015.
Advisory Action for U.S. Appl. No. 13/277,151, dated Aug. 19, 2014, 5 pages.
Appeal Brief for U.S. Appl. No. 12/953,282, filed Jul. 13, 2012, 17 pages.
Appeal Brief for U.S. Appl. No. 11/549,581, filed Mar. 7, 2013, 25 pages.
Appeal Brief for U.S. Appl. No. 11/549,591, filed Oct. 10, 2011, 20 pages.
Examiner's Answer to Appeal Brief for U.S. Appl. No. 11/549,591, dated Mar. 13, 2012, 12 pages.
Examiner's Answer to Appeal Brief for U.S. Appl. No. 12/953,282, dated Aug. 30, 2012, 6 pages.
Final Office Action for U.S. Appl. No. 11/549,596, dated Aug. 31, 2010, 10 pages.
Final Office Action for U.S. Appl. No. 11/549,599, dated Aug. 30, 2010, 10 pages.
Final Office Action for U.S. Appl. No. 12/953,282, dated Feb. 23, 2012, 12 pages.
Final Office Action for U.S. Appl. No. 13/277,151, dated Jun. 24, 2014, 22 pages.
Final Office Action for U.S. Appl. No. 11/549,581, dated Oct. 16, 2012, 28 pages.
Final Office Action for U.S. Appl. No. 11/549,591, dated Apr. 27, 2011, 11 pages.
Final Office Action for U.S. Appl. No. 11/549,596, dated Nov. 27, 2009, 10 pages.
Final Office Action for U.S. Appl. No. 11/549,599, dated Nov. 25, 2009, 14 pages.
Judgment, Entered Sep. 15 2015, Interference No. 106,031 Sep. 9, 2015, 3 pages.
Non-Final Office Action for U.S. Appl. No. 11/549,591, dated Dec. 9, 2008, 35 pages.
Non-Final Office Action for U.S. Appl. No. 11/549,599, dated May 4, 2012, 42 pages.
Non-Final Office Action for U.S. Appl. No. 13/109,728, dated Dec. 1, 2011, 16 pages.
Non-Final Office Action for U.S. Appl. No. 11/549,581, dated Jun. 22, 2012, 27 pages.
Non-Final Office Action for U.S. Appl. No. 11/549,591, dated May 12, 2010, 11 pages.
Non-Final Office Action for U.S. Appl. No. 11/549,591, dated Nov. 24, 2010, 10 pages.
Non-Final Office Action for U.S. Appl. No. 11/549,596, dated Mar. 17, 2010, 8 pages.
Non-Final Office Action for U.S. Appl. No. 11/549,596, dated May 21, 2012, 8 pages.
Non-Final Office Action for U.S. Appl. No. 11/549,596, dated Nov. 25, 2008, 29 pages.
Non-Final Office Action for U.S. Appl. No. 11/549,599, dated Aug. 28, 2012, 12 pages.
Non-Final Office Action for U.S. Appl. No. 11/549,599, dated Dec. 9, 2008, 35 pages.
Non-Final Office Action for U.S. Appl. No. 11/549,599, dated Mar. 17, 2010, 9 pages.
Non-Final Office Action for U.S. Appl. No. 11/549,605, dated Feb. 4, 2009, 11 pages.
Non-Final Office Action for U.S. Appl. No. 11/549,605, dated May 11, 2010, 16 pages.
Non-Final Office Action for U.S. Appl. No. 12/953,282, dated Jun. 7, 2011, 12 pages.
Non-Final Office Action for U.S. Appl. No. 13/277,151, dated Sep. 11, 2013, 18 pages.

(56) References Cited

OTHER PUBLICATIONS

Non-Final Office Action for U.S. Appl. No. 13/866,803, dated Jun. 13, 2013, 11 pages.
Non-Final Office Action for U.S. Appl. No. 13/866,803, dated Oct. 1, 2013, 11 pages.
Notice of Allowance for U.S. Appl. No. 11/549,596, dated Sep. 10, 2012, 5 pages.
Notice of Allowance for U.S. Appl. No. 11/549,599, dated Jan. 23, 2013, 7 pages.
Notice of Allowance for U.S. Appl. No. 11/549,605, dated Feb. 22, 2011, 4 pages.
Notice of Allowance for U.S. Appl. No. 11/549,605, dated Jan. 5, 2011, 4 pages.
Notice of Allowance for U.S. Appl. No. 13/109,728, dated Jun. 25, 2012, 7 pages.
Notice of Allowance for U.S. Appl. No. 13/277,151, dated Sep. 25, 2014, 10 pages.
Notice of Allowance for U.S. Appl. No. 13/866,803, dated Mar. 26, 2014, 11 pages.
Order-Miscellaneous, Entered Sep. 9, 2015; Interference No. 106,301, Sep. 9, 2015, 4 pages.
Patent Board Decision on Appeal for U.S. Appl. No. 11/549,591, dated Jun. 1, 2015, 10 pages.
Reply Brief for U.S. Appl. No. 11/549,591, filed May 8, 2012, 4 pages.
Reply Brief for U.S. Appl. No. 12/953,282, filed Oct. 29, 2012, 4 pages.
Terminal Disclaimer for U.S. Appl. No. 13/277,151, filed Sep. 12, 2014, 2 pages.
Vardy, et al., U.S. Appl. No. 13/669,242 entitled "Leadless Cardiac Pacemaker with Integral Battery and Redundant Welds", filed Nov. 5, 2012.
Webster, "Design of Cardiac Pacemakers", Chapter 11, 1995.
Notice of Allowance for U.S. Appl. No. 15/208,194, dated May 2, 2017.
Final Office Action for U.S. Appl. No. 15/208,194, dated Feb. 21, 2017.
Non-Final Office Action for U.S. Appl. No. 15/208,194, dated Sep. 22, 2016.
Beeby, et al., "Micromachined Silicon Generator for Harvesting Power from Vibrations," (Proceedings) PowerMEMS 2004, Nov. 28-30, 2004, Kyoto, Japan, 2004, pp. 104-107.
Bordacher, et al., "Impact and Prevention of Far-field Sensing in Fallback Mode Switches," Pacing and Clinical Electrophysiology, vol. 26, 2003, pp. 206-209.
Brandt, et al., "Far-field QRS Complex Sensing: Prevalence and Timing with Bipolar Atrial Leads," Pacing and Clinical Electrophysiology, vol. 23(3), 2000, pp. 315-320.
Brown, et al., "The Atomic Battery", Technology Review, Published by MIT, Jun. 16, 2005, 4 pages.
European Patent Office, "Communication of a Notice of Opposition for European Application No. 06836350.6", dated Oct. 24, 2014, 35 pages.
European Patent Office, "Extended European Search Report for Application No. European Application No. 06836350.6", dated Nov. 20, 2009.
European Patent Office, "Extended European Search Report for Application No. European Application No. 12159212.5", dated Jun. 4, 2012.
European Patent Office, "Extended European Search Report for Application No. European Application No. 12159213.3", dated Jun. 4, 2012.
European Patent Office, "Extended European Search Report for Application No. European Application No. 12159214.1", dated Jun. 4, 2012.
European Patent Office, "Extended European Search Report for Application No. European Application No. 12159218.2", dated Jun. 4, 2012.
European Patent Office, "Extended European Search Report for Application No. European Application No. 12159219.0", dated Jun. 6, 2012.
European Patent Office, "Extended European Search Report for Application No. European Application No. 12159220.8", dated Jun. 4, 2012.
European Patent Office, "Extended European Search Report for Application No. European Application No. 12159222.4", dated Jun. 4, 2012.
European Patent Office, "Extended European Search Report for Application No. European Application No. 12841426.5", dated Jun. 2, 2015.
International Preliminary Report on Patentability for Application No. PCT/US06/40564, dated Sep. 30, 2006, 26 pages.
Written Opinion for Application No. PCT/US06/40564, dated Apr. 8, 2008, 25 pages.
Notification of Transmittal of the International Search Report and the Written Opinion of the International Searching Authority, or the Declaration, International Application No. PCT/US12/57776, dated Jan. 10, 2013, 12 pages.
International Preliminary Report on Patentability for Application No. PCT/US12/57776, dated Apr. 22, 2014, 8 pages.
International Search Report for Application No. PCT/US06/40564, dated Apr. 8, 2008, 4 pages.
International Search Report for Application No. PCT/US12/57776, dated Jan. 10, 2013, 2 pages.
Written Opinion for Application No. PCT/US12/57776, dated Jan. 10, 2013, 7 pages.
Notification of Transmittal of the International Search Report and the Written Opinion of the International Searching Authority, or the Declaration, International Application No. PCT/US06/40564, dated Apr. 8, 2008, 29 pages.
Irnich, et al., "Do We Need Pacemakers Resistant to Magnetic Resonance Imaging?", Eurospace, vol. 7 (4), 2005, pp. 353-365.
Irnich, et al., "Electronic Security Systems and Active Implantable Medical Devices", Journal of Pacing and Clinical Electrophysiology, vol. 25 (8), 2002, pp. 1235-1258.
Jacobson, et al., U.S. Appl. No. 13/098,266 entitled "Rate Responsive Leadless Cardiac Pacemaker", filed Apr. 29, 2011.
Jacobson, et al., U.S. Appl. No. 12/953,282 entitled "Leadless Cardiac Pacemaker Triggered by Conductive Communication", filed Nov. 23, 2010.
Jacobson, et al., U.S. Appl. No. 13/109,728 entitled "Programmer for Biostimulator System", filed May 17, 2011.
Jacobson, et al., U.S. Appl. No. 13/191,229 entitled "Implantable Biostimulator Delivery System", filed Jul. 26, 2011.
Jacobson, et al., U.S. Appl. No. 13/277,151 entitled "Leadless Cardiac Pacemaker with Conducted Communication", filed Oct. 19, 2011.
Jacobson, et al., U.S. Appl. No. 13/708,732 entitled "Leadless Cardiac Pacemaker Triggered by Conductive Communication", filed Dec. 7, 2012.
Jacobson, et al., U.S. Appl. No. 13/866,803 entitled "Leadless Cardiac Pacemaker System for Usage in Combination with an Implantable Cardioverter-Defribrillator", filed Apr. 19, 2013.
Khairkhahan, et al., U.S. Appl. No. 13/331,922 entitled "Leadless Pacemaker with Radial Fixation Mechanism", filed Dec. 20, 2011.
Khairkhahan, et al., U.S. Appl. No. 13/272,074 entitled "Delivery Catheter Systems and Methods", filed Oct. 12, 2011.
Khairkhahan, et al., U.S. Appl. No. 13/272,082 entitled "Leadless Cardiac Pacemaker with Anti-Unscrewing Feature", filed Oct. 12, 2011.
Khairkhahan, et al., U.S. Appl. No. 13/324,781 entitled "Delivery Catheter Systems and Methods", filed Dec. 13, 2011.
Khairkhahan, et al., U.S. Appl. No. 13/324,802 entitled "Pacemaker Retrieval Systems and Methods", filed Dec. 13, 2011.
Luchinger, "Safety Aspects of Cardiac Pacemakers in Magnetic Resonance Imaging", A Dissertation Submitted to the Swiss Federal Institute of Technology Zurich, 2002, 137 pages.
Luechinger, et al., "Force and Torque Effects of a 1.5-Tesla MRI Scanner on Cardiac Pacemakers and ICDs," Journal of Pacing and Clinical Rlectrophysiology, vol. 24 (2), 2001, pp. 199-205.

(56) References Cited

OTHER PUBLICATIONS

Luechinger, et al., "In vivo Heating of Pacemaker Leads During Magnetic Resonance Imaging," European Heart Journal, vol. 26(4), 2005, pp. 376-383.
Nyenhuis, et al., "MRI and Implanted Medical Devices: Basic Interactions with an Emphasis on Heating," IEEE Transactions on Device and Materials Reliability, vol. 5(3), 2005, pp. 467-480.
Ostroff, et al., U.S. Appl. No. 12/568,513 entitled "MRI Compatible Leadless Cardiac Pacemaker", filed Sep. 28, 2009.
Ostroff, et al., U.S. Appl. No. 12/698,969 entitled "Leadless Cardiac Pacemaker with Secondary Fixation Capability", filed Feb. 2, 2010.
Ostroff, et al., U.S. Appl. No. 13/272,092 entitled "Temperature Sensor for a Leadless Cardiac Pacemaker", filed Oct. 12, 2011.
Ostroff, et al., U.S. Appl. No. 13/910,896 entitled "Leadless Pacemaker with Multiple Electrodes", filed Jun. 5, 2013.
Ostroff, et al., U.S. Appl. No. 13/915,560 entitled "MRI Compatible Leadless Cardiac Pacemaker", filed Jun. 11, 2013.
Pertijs, et al., U.S. Appl. No. 13/901,414 entitled "Temperature Sensor for a Leadless Cardiac Pacemaker", filed May 23, 2013.
Poore, et al., U.S. Appl. No. 10/891,747 entitled "System and Method for Synchronizing Supplemental Pacing Pulses Generated by a Satellite Pacing Device with Primary Pulses Delivered by a Separate Pacing Device", filed Jun. 14, 2004.
Shellock, et al., "Cardiac Pacemaker: in vitro Assessment at 1.5 T," American Heart Journal, vol. 151(2), 2006, pp. 436-443.
Pacesetter Request for Adverse Judgment, Interference No. 106,031 Sep. 10, 2015, 3 pages.
Response to Non-Final Office Action for U.S. Appl. No. 12/953,282, dated Dec. 22, 2011, 9 pages.

\* cited by examiner

LEADLESS CARDIAC PACEMAKER SYSTEM FOR USAGE IN COMBINATION WITH AN IMPLANTABLE CARDIOVERTER-DEFIBRILLATOR

CROSS REFERENCE TO RELATED APPLICATIONS

This application is a divisional of U.S. patent application Ser. No. 15/596,290, filed May 16, 2017, which is a divisional of U.S. patent application Ser. No. 15/208,194, filed Jul. 12, 2016, now U.S. Pat. No. 9,687,666, which is a continuation of U.S. patent application Ser. No. 14/885,853, filed Oct. 16, 2015, now U.S. Pat. No. 9,409,033, which is a divisional of U.S. patent application Ser. No. 14/318,201, filed Jun. 27, 2014, now U.S. Pat. No. 9,192,774, which is a divisional of U.S. patent application Ser. No. 13/866,803, filed Apr. 19, 2013, now U.S. Pat. No. 8,798,745, which is a divisional of U.S. patent application Ser. No. 11/549,599, filed Oct. 13, 2006, now U.S. Pat. No. 8,457,742, which application claims the benefit of priority to and incorporates herein by reference in its entirety for all purposes, U.S. Provisional Patent Application Nos. 60/726,706 entitled "LEADLESS CARDIAC PACEMAKER WITH CONDUCTED COMMUNICATION," filed Oct. 14, 2005; 60/761,531 entitled "LEADLESS CARDIAC PACEMAKER DELIVERY SYSTEM," filed Jan. 24, 2006; 60/729,671 entitled "LEADLESS CARDIAC PACEMAKER TRIGGERED BY CONDUCTED COMMUNICATION," filed Oct. 24, 2005; 60/737,296 entitled "SYSTEM OF LEADLESS CARDIAC PACEMAKERS WITH CONDUCTED COMMUNICATION," filed Nov. 16, 2005; 60/739,901 entitled "LEADLESS CARDIAC PACEMAKERS WITH CONDUCTED COMMUNICATION FOR USE WITH AN IMPLANTABLE CARDIOVERTER-DEFIBRILLATOR," filed Nov. 26, 2005; 60/749,017 entitled "LEADLESS CARDIAC PACEMAKER WITH CONDUCTED COMMUNICATION AND RATE RESPONSIVE PACING," filed Dec. 10, 2005; and 60/761,740 entitled "PROGRAMMER FOR A SYSTEM OF LEADLESS CARDIAC PACEMAKERS WITH CONDUCTED COMMUNICATION," filed Jan. 24, 2006; all by Peter M. Jacobson.

BACKGROUND

Cardiac pacing electrically stimulates the heart when the heart's natural pacemaker and/or conduction system fails to provide synchronized atrial and ventricular contractions at appropriate rates and intervals for a patient's needs. Such bradycardia pacing provides relief from symptoms and even life support for hundreds of thousands of patients. Cardiac pacing may also give electrical overdrive stimulation intended to suppress or convert tachyarrhythmias, again supplying relief from symptoms and preventing or terminating arrhythmias that could lead to sudden cardiac death.

Cardiac pacing is usually performed by a pulse generator implanted subcutaneously or sub-muscularly in or near a patient's pectoral region. Implantable cardioverter-defibrillator (ICD) pulse generators usually include cardiac pacing functions, both for bradycardia support and for overdrive stimulation. The generator usually connects to the proximal end of one or more implanted leads, the distal end of which contains one or more electrodes for positioning adjacent to the inside or outside wall of a cardiac chamber. The leads have an insulated electrical conductor or conductors for connecting the pulse generator to electrodes in the heart. Such electrode leads typically have lengths of 50 to 70 centimeters.

A conventional pulse generator may be connected to more than one electrode-lead. For example, atrio-ventricular pacing, also commonly called dual-chamber pacing, involves a single pulse generator connected to one electrode-lead usually placed in the right atrium and a second electrode-lead usually placed in the right ventricle. Such a system can electrically sense heartbeat signals and deliver pacing pulses separately in each chamber. In typical use, the dual-chamber pacing system paces the atrium if no atrial heartbeat is sensed since a predetermined time, and then paces the ventricle if no ventricular heartbeat is sensed within a predetermined time after the natural or paced atrial beat. Such pulse generators can also alter the timing of atrial and ventricular pacing pulses when sensing a ventricular beat that is not preceded by an atrial beat within a predetermined time; that is, a ventricular ectopic beat or premature ventricular contraction. Consequently, dual-chamber pacing involves pacing and sensing in an atrium and a ventricle, and internal communication element so that an event in either chamber can affect timing of pacing pulses in the other chamber.

Recently, left-ventricular cardiac pacing has been practiced to ameliorate heart failure; a practice termed cardiac resynchronization therapy (CRT). CRT has been practiced with electrode-leads and a pulse generator, either an implantable cardioverter-defibrillator (CRT-D) or an otherwise conventional pacemaker (CRT-P). The left-ventricular pacing conventionally uses an electrode in contact with cardiac muscle in that chamber. The corresponding electrode-lead is usually placed endocardially in a transvenous manner through the coronary sinus vein, or epicardially. Left-ventricular pacing is usually practiced together with right-atrial and right-ventricular pacing with a single implanted pulse generator connected to three electrode-leads. CRT pulse generators can independently vary the time between an atrial event and right-ventricular pacing, and the time between an atrial event and left-ventricular pacing, so that the left ventricular pacing pulse can precede, follow, or occur at the same time as the right-ventricular pacing pulse. Similarly to dual-chamber pacing, systems with left-ventricular pacing also change atrial and ventricular pacing timing in response to premature ventricular contractions. Consequently, CRT-D involves pacing in an atrium and in two ventricles, sensing in the atrium and at least one ventricle, and an internal communication element so that an event in the atrium can affect timing of pacing pulses in each ventricle, and an internal communication element so that an event in at least one ventricle can affect timing of pacing pulses in the atrium and the other ventricle.

Pulse generator parameters are usually interrogated and modified by a programming device outside the body, via a loosely-coupled transformer with one inductance within the body and another outside, or via electromagnetic radiation with one antenna within the body and another outside.

Although more than one hundred thousand ICD and CRT-D systems are implanted annually, several problems are known.

A conventional pulse generator has an interface for connection to and disconnection from the electrode leads that carry signals to and from the heart. Usually at least one male connector molding has at least one additional terminal pin not required for defibrillation functions at the proximal end of the electrode lead. The at least one male connector mates with at least one corresponding female connector molding and terminal block within the connector molding at the pulse generator. Usually a setscrew is threaded in at least one terminal block per electrode lead to secure the connection electrically and mechanically. One or more O-rings usually are also supplied to help maintain electrical isolation between the connector moldings. A setscrew cap or slotted cover is typically included to provide electrical insulation of the setscrew. The complex connection between connectors and leads provides multiple opportunities for malfunction.

For example, failure to introduce the lead pin completely into the terminal block can prevent proper connection between the generator and electrode.

Failure to insert a screwdriver correctly through the setscrew slot, causing damage to the slot and subsequent insulation failure.

Failure to engage the screwdriver correctly in the setscrew can cause damage to the setscrew and preventing proper connection.

Failure to tighten the setscrew adequately also can prevent proper connection between the generator and electrode, however over-tightening of the setscrew can cause damage to the setscrew, terminal block, or lead pin, and prevent disconnection if necessary for maintenance.

Fluid leakage between the lead and generator connector moldings, or at the setscrew cover, can prevent proper electrical isolation.

Insulation or conductor breakage at a mechanical stress concentration point where the lead leaves the generator can also cause failure.

Inadvertent mechanical damage to the attachment of the connector molding to the generator can result in leakage or even detachment of the molding.

Inadvertent mechanical damage to the attachment of the connector molding to the lead body, or of the terminal pin to the lead conductor, can result in leakage, an open-circuit condition, or even detachment of the terminal pin and/or molding.

The lead body can be cut inadvertently during surgery by a tool, or cut after surgery by repeated stress on a ligature used to hold the lead body in position. Repeated movement for hundreds of millions of cardiac cycles can cause lead conductor breakage or insulation damage anywhere along the lead body.

Although leads are available commercially in various lengths, in some conditions excess lead length in a patient exists and is to be managed. Usually the excess lead is coiled near the pulse generator. Repeated abrasion between the lead body and the generator due to lead coiling can result in insulation damage to the lead.

Friction of the lead against the clavicle and the first rib, known as subclavian crush, can result in damage to the lead.

In dual-chamber pacing in an ICD, and in CRT-D, multiple leads are implanted in the same patient and sometimes in the same vessel. Abrasion between these leads for hundreds of millions of cardiac cycles can cause insulation breakdown or even conductor failure.

Subcutaneous ICDs that do not use endocardial, transvenous or epicardial lead wires, can deliver defibrillation using subcutaneous electrodes. However, pacing the heart from subcutaneous electrodes results in diaphragmatic stimulation which is uncomfortable to the patient if used in long-term therapy. Therefore pacing therapies such as bradycardia pacing therapy, anti-tachycardia therapy, atrial overdrive pacing for the prevention of arrhythmias, dual chamber pacing for atrio-ventricular synchronization and CRT therapies are inappropriate.

SUMMARY

According to an embodiment of a cardiac pacing system, one or more leadless cardiac pacemakers are configured for implantation in electrical contact with a cardiac chamber and configured for performing cardiac pacing functions in combination with a co-implanted implantable cardioverter-defibrillator (ICD). The leadless cardiac pacemaker comprises at least two leadless electrodes configured for delivering cardiac pacing pulses, sensing evoked and/or natural cardiac electrical signals, and bidirectionally communicating with the co-implanted ICD.

BRIEF DESCRIPTION OF THE DRAWINGS

Embodiments of the invention relating to both structure and method of operation may best be understood by referring to the following description and accompanying drawings, in which similar reference characters denote similar elements throughout the several views.

DETAILED DESCRIPTION

Figure 1A:
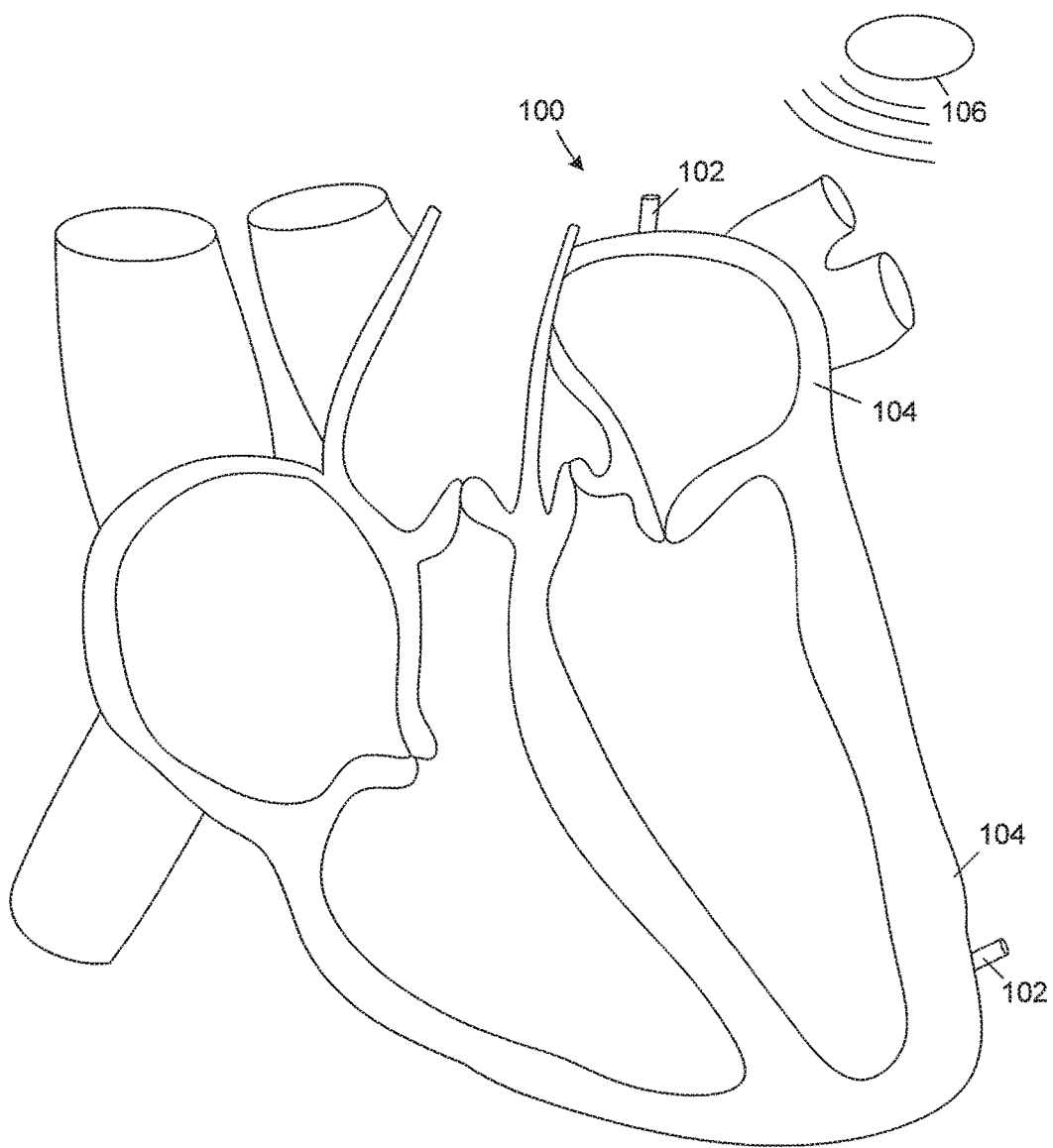
FIG. 1A is a pictorial diagram showing an embodiment of a cardiac pacing system including one or more leadless cardiac pacemakers with conducted communication for performing cardiac pacing in conjunction with an implantable cardioverter-defibrillator (ICD)

In some embodiments of an illustrative cardiac pacing system, one or more leadless cardiac pacemakers with low-power conducted communication can perform single-chamber pacing, dual-chamber pacing, CRT-D, or other pacing, co-implanted with an ICD, enabling functionality extending beyond what is possible or appropriate for conventional subcutaneous ICDs.

A system of leadless cardiac pacemakers enables pacing in conjunction with an implantable cardioverter-defibrillator (ICD) for usage in single-chamber, dual-chamber, CRT-D, and other multi-chamber cardiac pacing schemes.

Various embodiments of a system of an implantable cardioverter-defibrillator (ICD) and one or more leadless cardiac pacemakers are described. The individual leadless cardiac pacemakers can be substantially enclosed in a hermetic housing suitable for placement on or attachment to the inside or outside of a cardiac chamber. The pacemaker can have at least two electrodes located within, on, or near the housing, for delivering pacing pulses to and sensing electrical activity from the muscle of the cardiac chamber, and for bidirectional communication with at least one other co-implanted leadless cardiac pacemaker and optionally with another device outside the body. The housing can contain a primary battery to provide power for pacing, sensing, and communication. The housing can also contain circuits for sensing cardiac activity from the electrodes, receiving information from at least one other device via the electrodes, generating pacing pulses for delivery via the electrodes, transmitting information to at least one other device via the electrodes, monitoring device health, and controlling these operations in a predetermined manner.

A cardiac pacing system includes cardiac pacing in conjunction with an ICD and can supplement the functionality of ICDs with cardiac pacing functions, extending beyond functionality of conventional ICD-pacing arrangements.

The cardiac pacing system comprises a leadless cardiac pacemaker or pacemakers adapted to perform cardiac pacing functions with a co-implanted ICD, without a pacing electrode-lead separate from the leadless cardiac pacemaker, without a communication coil or antenna in the leadless cardiac pacemaker, and without an additional requirement on battery power in the leadless cardiac pacemaker for transmitted communication.

In some embodiments, a cardiac pacing system comprises an ICD with one or more leadless pacemakers for implantation adjacent to the inside or outside wall of a cardiac chamber, without the need for a connection between the leadless pulse generator and an electrode lead that can be connected or disconnected during implantation and repair procedures, and without the need for a lead body.

In some embodiments of a cardiac pacing system, communication between the implanted leadless cardiac pacemaker or pacemakers and other devices, including any co-implanted leadless cardiac pacemakers, the co-implanted ICD, and optionally a device external to the body, uses conducted communication via the same electrodes used for pacing, without the need for an antenna or telemetry coil.

Some embodiments and/or arrangements can implement communication between an implanted leadless cardiac pacemaker and other devices with power requirements similar to those for cardiac pacing, to enable optimization of battery performance. For example, transmission from the leadless cardiac pacemaker adds no power while reception adds a limited amount of power, such as about 25 microwatt.

A cardiac pacemaker or pacemakers are adapted for implantation in the human body. In a specific embodiment, one or more leadless cardiac pacemakers can be co-implanted with an implantable cardioverter-defibrillator (ICD). Each leadless cardiac pacemaker uses two or more electrodes located within, on, or within two centimeters of the housing of the pacemaker, for pacing and sensing at the cardiac chamber, for bidirectional communication with the ICD, optionally with at least one other leadless cardiac pacemaker, and optionally with at least one other device outside the body.

Referring to FIG. 1A, a pictorial diagram shows an embodiment of a cardiac pacing system 100 including one or more leadless cardiac pacemakers 102 with conducted communication for performing cardiac pacing in conjunction with an implantable cardioverter-defibrillator (ICD) 106. The system 100 can implement for example single-chamber pacing, dual-chamber pacing, or three-chamber pacing for cardiac resynchronization therapy, without requiring pacing lead connections to the defibrillator 106. The illustrative cardiac pacing system 100 comprises at least one leadless cardiac pacemaker 102 configured for implantation in electrical contact with a cardiac chamber 104 and configured to perform cardiac pacing functions in combination with a co-implanted implantable cardioverter-defibrillator (ICD) 106. One or more of the leadless cardiac pacemakers 102 can comprise at least two leadless electrodes 108 configured for delivering cardiac pacing pulses, sensing evoked and/or natural cardiac electrical signals, and uni-directionally or bi-directionally communicating with the co-implanted ICD 106.

The leadless cardiac pacemakers 102 can communicate with one another and/or communicate with a non-implanted programmer and/or the implanted ICD 106 via the same electrodes 108 that are also used to deliver pacing pulses. Usage of the electrodes 108 for communication enables the one or more leadless cardiac pacemakers 102 for antenna-less and telemetry coil-less communication.

The leadless cardiac pacemakers 102 can be configured to communicate with one another and to communicate with a non-implanted programmer 106 via communication that has outgoing communication power requirements essentially met by power consumed in cardiac pacing.

Figure 1B:
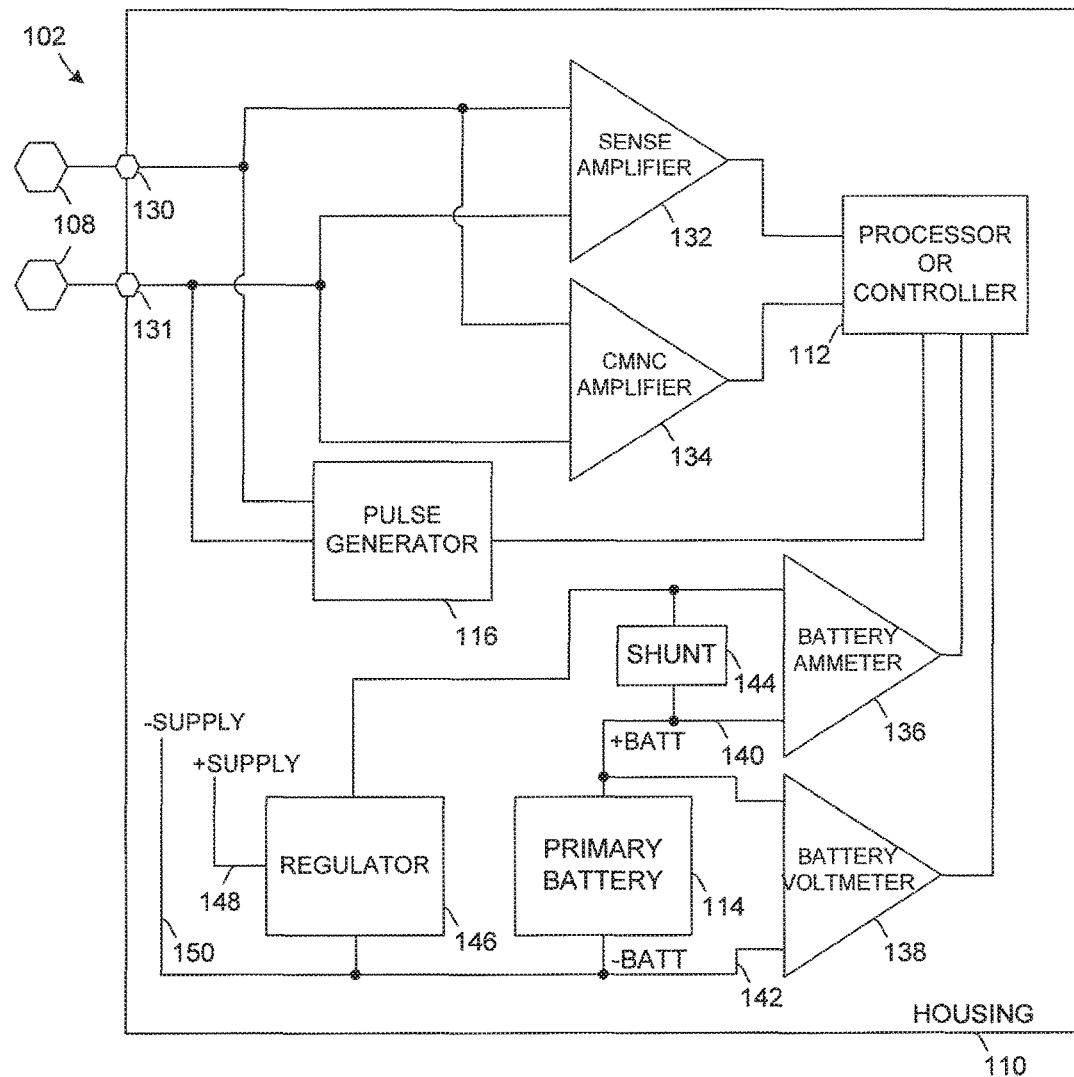
FIG. 1B is a schematic block diagram showing interconnection of operating elements of an embodiment of a leadless cardiac pacemaker that can be used in cardiac pacing system including one or more leadless cardiac pacemakers and an implantable cardioverter-defibrillator (ICD)

In some embodiments, the individual leadless cardiac pacemaker 102 can comprise a hermetic housing 110 configured for placement on or attachment to the inside or outside of a cardiac chamber 104 and at least two leadless electrodes 108 proximal to the housing 110 and configured for bidirectional communication with at least one other device 106 within or outside the body. For example, FIG. 1B depicts a single leadless cardiac pacemaker 102 and shows the pacemaker's functional elements substantially enclosed in a hermetic housing 110. The pacemaker 102 has at least two electrodes 108 located within, on, or near the housing 110, for delivering pacing pulses to and sensing electrical activity from the muscle of the cardiac chamber, and for bidirectional communication with at least one other device within or outside the body. Hermetic feedthroughs 130, 131 conduct electrode signals through the housing 110. The housing 110 contains a primary battery 114 to supply power for pacing, sensing, and communication. The housing 110 also contains circuits 132 for sensing cardiac activity from the electrodes 108, circuits 134 for receiving information from at least one other device via the electrodes 108, and a pulse generator 116 for generating pacing pulses for delivery via the electrodes 108 and also for transmitting information to at least one other device via the electrodes 108. The housing 110 can further contain circuits for monitoring device health, for example a battery current monitor 136 and a battery voltage monitor 138, and can contain circuits 112 for controlling operations in a predetermined manner.

The one or more leadless electrodes 108 can be configured to communicate bidirectionally among the multiple leadless cardiac pacemakers and/or the implanted ICD to coordinate pacing pulse delivery using messages that identify an event at an individual pacemaker originating the message and a pacemaker receiving the message react as directed by the message depending on the origin of the message. A pacemaker or pacemakers that receive the message react as directed by the message depending on the message origin or location. In some embodiments or conditions, the two or more leadless electrodes 108 can be configured to communicate bidirectionally among the one or more leadless cardiac pacemakers 102 and/or the ICD 106 and transmit data including designated codes for events detected or created by an individual pacemaker. Individual pacemakers can be configured to issue a unique code corresponding to an event type and a location of the sending pacemaker.

Information communicated on the incoming communication channel can include but is not limited to pacing rate, pulse duration, sensing threshold, and other parameters commonly programmed externally in conventional pacemakers. Information communicated on the outgoing communication channel can include but is not limited to programmable parameter settings, pacing and sensing event counts, battery voltage, battery current, device health, and other information commonly displayed by external programmers used with conventional pacemakers. The outgoing communication channel can also echo information from the incoming channel, to confirm correct programming.

In some embodiments, information encoded on the leadless cardiac pacemakers can be used to enhance the sensitivity and specificity of the ICD such as, for example, a subcutaneous-only implantable defibrillator. Illustratively, a subcutaneously-only defibrillator senses only far-field signals, making difficult extraction of atrial information as well as uniquely identifying atrial depolarization from ventricular depolarization. When a subcutaneous-only defibrillator is used in combination with one or more leadless cardiac pacemakers, the information derived from the pacing pulse for each leadless pacemaker can be gathered and used to identify atrial and ventricular depolarization without ambiguity.

The leadless cardiac pacemaker 102 can communicate the information listed hereinabove with the implanted ICD 106, or with a programmer outside the body, or both.

For example, in some embodiments an individual pacemaker 102 of the one or more leadless cardiac pacemakers can be configured to deliver a coded pacing pulse with a code assigned according to pacemaker location and configured to transmit a message to one or more other leadless cardiac pacemakers via the coded pacing pulse wherein the code identifies the individual pacemaker originating an event. The pacemaker or pacemakers receiving the message are adapted to respond to the message in a predetermined manner depending on type and location of the event.

In some embodiments or conditions, individual pacemakers 102 can deliver a coded pacing pulse with a code assigned according to pacemaker location and configured to transmit a message to at least one of the leadless cardiac pacemakers via the coded pacing pulse wherein the code identifies the individual pacemaker originating an event. The individual pacemakers can be further configured to deliver a pacing pulse in absence of encoding whereby, for dual-chamber cardiac pacing, a pacing pulse that is not generated in a first cardiac pacemaker that senses the pacing pulse is necessarily generated in a second cardiac pacemaker. Accordingly, neither the use of a code to identify the chamber corresponding to a pacing pulse, nor the use of a code to identify the type of pulse (whether paced or sensed) is a necessary step in a simple system such as a dual chamber pacing system disclosed in the specification.

Moreover, information communicated on the incoming channel can also include a message from another leadless cardiac pacemaker signifying that the other leadless cardiac pacemaker has sensed a heartbeat or has delivered a pacing pulse, and identifies the location of the other pacemaker. Similarly, information communicated on the outgoing channel can also include a message to another leadless cardiac pacemaker or pacemakers, or to the ICD, that the sending leadless cardiac pacemaker has sensed a heartbeat or has delivered a pacing pulse at the location of the sending pacemaker.

In some embodiments and in predetermined conditions, an individual pacemaker 102 of the one or more leadless cardiac pacemakers can be configured to communicate to one or more other implanted pacemakers indication of the occurrence of a sensed heartbeat at the individual pacemaker location via generation of a coded pacing pulse triggered by the sensed heartbeat in a natural refractory period following the sensed heartbeat.

Referring again to FIGS. 1A and 1B, in various embodiments a cardiac pacing system 100 comprises at least one leadless cardiac pacemaker 102 that is configured for implantation in electrical contact with a cardiac chamber 104 and configured to perform cardiac pacing functions in combination with a co-implanted implantable cardioverter-defibrillator (ICD) 106.

An embodiment of a cardiac pacing system 100 comprises an implantable cardioverter-defibrillator (ICD) 106 and at least one leadless cardiac pacemaker 102 configured for implantation in electrical contact with a cardiac chamber and for performing cardiac rhythm management functions in combination with the implantable ICD 106. The implantable ICD 106 and the one or more leadless cardiac pacemakers 102 configured for leadless intercommunication by information conduction through body tissue.

In another embodiment, a cardiac pacing system 100 comprises one or more leadless cardiac pacemaker 102 or pacemakers configured for implantation in electrical contact with a cardiac chamber 104 and configured to perform cardiac pacing functions in combination with a co-implanted implantable cardioverter-defibrillator (ICD) 106. The leadless cardiac pacemaker or pacemakers 102 are configured to intercommunicate and/or to communicate with a non-implanted programmer and/or the implanted ICD 106 via two or more electrodes 108 that are used for delivering pacing pulses. The pacemakers 102 are configured for antenna-less and telemetry coil-less communication.

In a further embodiment, a cardiac pacing system 100 comprises at least one leadless cardiac pacemaker 102 configured for implantation in electrical contact with a cardiac chamber 104 and configured to perform cardiac pacing functions in combination with a co-implanted implantable cardioverter-defibrillator (ICD) 106. The leadless cardiac pacemaker or pacemakers 102 comprise at least two leadless electrodes 108 configured for delivering cardiac pacing pulses, sensing evoked and/or natural cardiac electrical signals, and transmitting information to the co-implanted ICD 106.

In another example embodiment, a cardiac pacing system 100 comprises at least one leadless cardiac pacemaker 102 configured for implantation in electrical contact with a cardiac chamber 104 and configured to perform cardiac pacing functions in combination with a co-implanted implantable cardioverter-defibrillator (ICD) 106. The leadless cardiac pacemaker or pacemakers 102 comprising at least two leadless electrodes 108 configured for delivering cardiac pacing pulses, sensing evoked and/or natural cardiac electrical signals, and receiving information from the co-implanted ICD 106.

As shown in the illustrative embodiments, a leadless cardiac pacemaker 102 can comprise two or more leadless electrodes 108 configured for delivering cardiac pacing pulses, sensing evoked and/or natural cardiac electrical signals, and bidirectionally communicating with the co-implanted ICD 106. A leadless cardiac pacemaker 102 can be configured to communicate with other pacemakers and/or communicate with a non-implanted programmer via communication that has communication power requirements essentially met by power consumed in cardiac pacing. For example, the leadless cardiac pacemaker 102 can be configured to communicate with other pacemakers and with a non-implanted programmer via communication that has negligible transmission power requirements in addition to power consumed in cardiac pacing.

Individual pacemakers of the one or more leadless cardiac pacemakers 102 can be configured for operation in a particular location and a particular functionality at manufacture and/or at programming by an external programmer. Bidirectional communication among the multiple leadless cardiac pacemakers can be arranged to communicate notification of a sensed heartbeat or delivered pacing pulse event and encoding type and location of the event to another implanted pacemaker or pacemakers. The pacemaker or pacemakers receiving the communication decode the information and respond depending on location of the receiving pacemaker and predetermined system functionality.

In some embodiments, individual pacemakers 102 of the one or more leadless cardiac pacemakers can be configured to receive conducted communication from a co-implanted cardioverter-defibrillator (ICD) 106 that configures the pacemakers 102 to deliver overdrive anti-tachycardia pacing in response to a detected tachyarrhythmia.

Also shown in FIG. 1B, the primary battery 114 has positive terminal 140 and negative terminal 142. A suitable primary battery has an energy density of at least 3 Wh/cc, a power output of 70 microwatts, a volume less than 1 cubic centimeter, and a lifetime greater than 5 years.

One suitable primary battery uses beta-voltaic technology, licensed to BetaBatt Inc. of Houston, Tex., USA, and developed under a trade name DEC™ Cell, in which a silicon wafer captures electrons emitted by a radioactive gas such as tritium. The wafer is etched in a three-dimensional surface to capture more electrons. The battery is sealed in a hermetic package which entirely contains the low-energy particles emitted by tritium, rendering the battery safe for long-term human implant from a radiological-health standpoint. Tritium has a half-life of 12.3 years so that the technology is more than adequate to meet a design goal of a lifetime exceeding 5 years.

Current from the positive terminal 140 of primary battery 114 flows through a shunt 144 to a regulator circuit 146 to create a positive voltage supply 148 suitable for powering the remaining circuitry of the pacemaker 102. The shunt 144 enables the battery current monitor 136 to provide the processor 112 with an indication of battery current drain and indirectly of device health.

The illustrative power supply can be a primary battery 114 such as a beta-voltaic converter that obtains electrical energy from radioactivity. In some embodiments, the power supply can be selected as a primary battery 114 that has a volume less than approximately 1 cubic centimeter.

The leadless cardiac pacemaker or pacemakers 102 can be configured to detect a natural cardiac depolarization, time a selected delay interval, and deliver an information-encoded pulse during a refractory period following the natural cardiac depolarization. By encoding information in a pacing pulse, power consumed for transmitting information is not significantly greater than the power used for pacing. Information can be transmitted through the communication channel with no separate antenna or telemetry coil. Communication bandwidth is low with only a small number of bits encoded on each pulse.

In some embodiments, information can be encoded using a technique of gating the pacing pulse for very short periods of time at specific points in the pacing pulse. During the gated sections of the pulse, no current flows through the electrodes of a leadless cardiac pacemaker. Timing of the gated sections can be used to encode information. The specific length of a gated segment depends on the programmer's ability to detect the gated section. A certain amount of smoothing or low-pass filtering of the signal can be expected from capacitance inherent in the electrode/skin interface of the programmer as well as the electrode/tissue interface of the leadless cardiac pacemaker. A gated segment is set sufficiently long in duration to enable accurate detection by the programmer, limiting the amount of information that can be transmitted during a single pacing pulse. Accordingly, a technique for communication can comprise generating stimulation pulses on stimulating electrodes of an implanted biostimulator and encoding information onto generated stimulation pulses. Encoding information onto the pulses can comprise gating the stimulation pulses for selected durations at selected timed sections in the stimulation pulses whereby gating removes current flow through the stimulating electrodes and timing of the gated sections encodes the information.

Another method of encoding information on pacing pulses involves varying the timing between consecutive pacing pulses in a pulse sequence. Pacing pulses, unless inhibited or triggered, occur at predetermined intervals. The interval between any two pulses can be varied slightly to impart information on the pulse series. The amount of information, in bits, is determined by the time resolution of the pulse shift. The steps of pulse shifting are generally on the order of microseconds. Shifting pulses by up to several milliseconds does not have an effect on the pacing therapy and cannot be sensed by the patient, yet significant information can be transmitted by varying pulse intervals within the microsecond range. The method of encoding information in variation of pulses is less effective if many of the pulses are inhibited or triggered. Accordingly, a technique for communication can comprise generating stimulation pulses on stimulating electrodes of an implanted biostimulator and encoding information onto generated stimulation pulses comprising selectively varying timing between consecutive stimulation pulses.

Alternatively or in addition to encoding information in gated sections and/or pulse interval, overall pacing pulse width can be used to encode information.

The three described methods of encoding information on pacing pulses can use the programmer to distinguish pacing pulses from the patient's normal electrocardiogram, for example by recognition of the specific morphology of the pacing pulse compared to the R-wave generated during the cardiac cycle. For example, the external programmer can be adapted to distinguish a generated cardiac pacing pulse from a natural cardiac depolarization in an electrocardiogram by performing comparative pattern recognition of a pacing pulse and an R-wave produced during a cardiac cycle.

In an illustrative embodiment, the primary battery 114 can be selected to source no more than 70 microwatts instantaneously since a higher consumption may cause the voltage across the battery terminals to collapse. Accordingly in one illustrative embodiment the circuits depicted in FIG. 1B can be designed to consume no more than a total of 64 microwatts. The design avoids usage of a large filtering capacitor for the power supply or other accumulators such as a supercapacitor or rechargeable secondary cell to supply peak power exceeding the maximum instantaneous power capability of the battery, components that would add volume and cost.

In various embodiments, the system can manage power consumption to draw limited power from the battery, thereby reducing device volume. Each circuit in the system can be designed to avoid large peak currents. For example, cardiac pacing can be achieved by discharging a tank capacitor (not shown) across the pacing electrodes. Recharging of the tank capacitor is typically controlled by a charge pump circuit. In a particular embodiment, the charge pump circuit is throttled to recharge the tank capacitor at constant power from the battery.

Implantable systems that communicate via long distance radio-frequency (RF) schemes, for example Medical Implant Communication Service (MICS) transceivers, which exhibit a peak power requirement on the order of 10 milliwatts, and other RF or inductive telemetry schemes are unable to operate without use of an additional accumulator. Moreover, even with the added accumulator, sustained operation would ultimately cause the voltage across the battery to collapse.

In some embodiments, the controller 112 in one leadless cardiac pacemaker 102 can access signals on the electrodes 108 and can examine output pulse duration from another pacemaker for usage as a signature for determining triggering information validity and, for a signature arriving within predetermined limits, activating delivery of a pacing pulse following a predetermined delay of zero or more milliseconds. The predetermined delay can be preset at manufacture, programmed via an external programmer, or determined by adaptive monitoring to facilitate recognition of the triggering signal and discriminating the triggering signal from noise. In some embodiments or in some conditions, the controller 112 can examine output pulse waveform from another leadless cardiac pacemaker for usage as a signature for determining triggering information validity and, for a signature arriving within predetermined limits, activating delivery of a pacing pulse following a predetermined delay of zero or more milliseconds.

Figure 2:
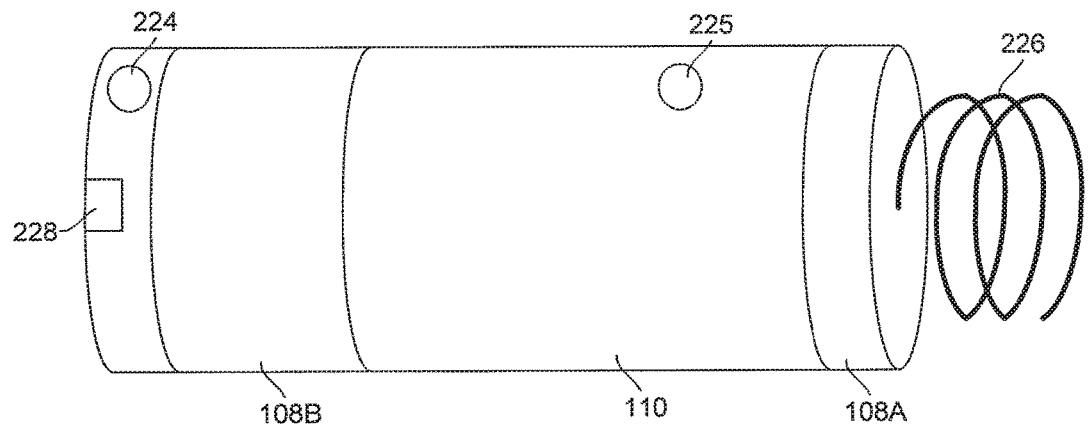
FIG. 2 is a pictorial diagram showing the physical location of some elements of an embodiment of a leadless biostimulator that can be used as part of a multi-chamber cardiac pacing system.

Also shown in FIG. 2, a cylindrical hermetic housing 110 is shown with annular electrodes 108 at housing extremities. In the illustrative embodiment, the housing 110 can be composed of alumina ceramic which provides insulation between the electrodes. The electrodes 108 are deposited on the ceramic, and are platinum or platinum-iridium.

Several techniques and structures can be used for attaching the housing 110 to the interior or exterior wall of cardiac chamber muscle 104.

A helix 226 and slot 228 enable insertion of the device endocardially or epicardially through a guiding catheter. A screwdriver stylet can be used to rotate the housing 110 and force the helix 226 into muscle 104, thus affixing the electrode 108A in contact with stimulable tissue. Electrode 108B serves as an indifferent electrode for sensing and pacing. The helix 226 may be coated for electrical insulation, and a steroid-eluting matrix may be included near the helix to minimize fibrotic reaction, as is known in conventional pacing electrode-leads.

In other configurations, suture holes 224 and 225 can be used to affix the device directly to cardiac muscle with ligatures, during procedures where the exterior surface of the heart is exposed.

Other attachment structures used with conventional cardiac electrode-leads including tines or barbs for grasping trabeculae in the interior of the ventricle, atrium, or coronary sinus may also be used in conjunction with or instead of the illustrative attachment structures.

Figure 3:
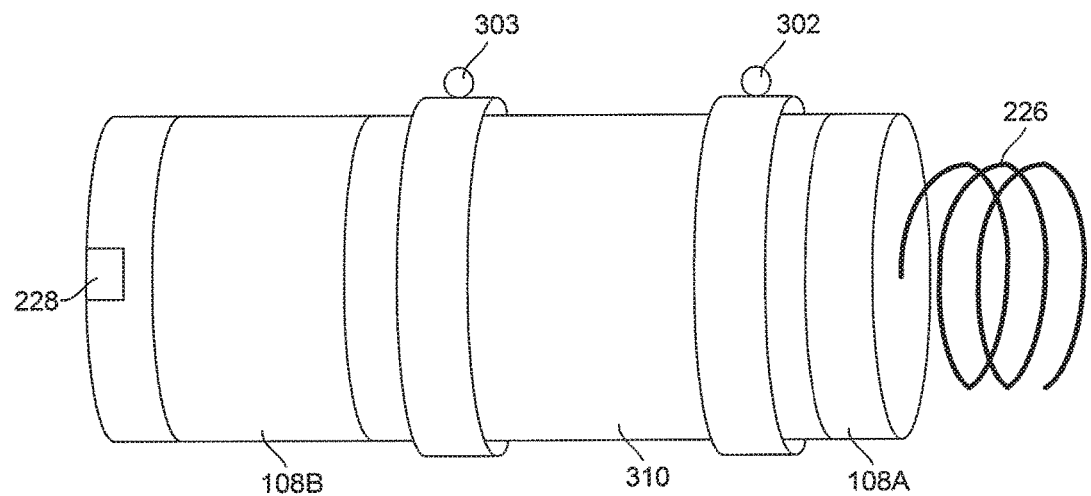
FIG. 3 is a pictorial diagram that depicts the physical location of some elements in an alternative embodiment of a leadless biostimulator that can be used as part of a multi-chamber cardiac pacing system.

Referring to FIG. 3, a pictorial view shows another embodiment of a single leadless cardiac pacemaker 102 that can be used in a cardiac pacing system 100 with at least one other pacemaker. The leadless cardiac pacemaker 102 includes a cylindrical metal housing 310 with an annular electrode 108A and a second electrode 108B. Housing 310 can be constructed from titanium or stainless steel. Electrode 108A can be constructed using a platinum or platinum-iridium wire and a ceramic or glass feed-thru to provide electrical isolation from the metal housing. The housing can be coated with a biocompatible polymer such as medical grade silicone or polyurethane except for the region outlined by electrode 108B. The distance between electrodes 108A and 108B should be approximately 1 cm to optimize sensing amplitudes and pacing thresholds. A helix 226 and slot 228 can be used for insertion of the device endocardially or epicardially through a guiding catheter. In addition, suture sleeves 302 and 303 made from silicone can be used to affix to the device directly to cardiac muscle with ligatures, for example in an epicardial or other application.

Figure 4:
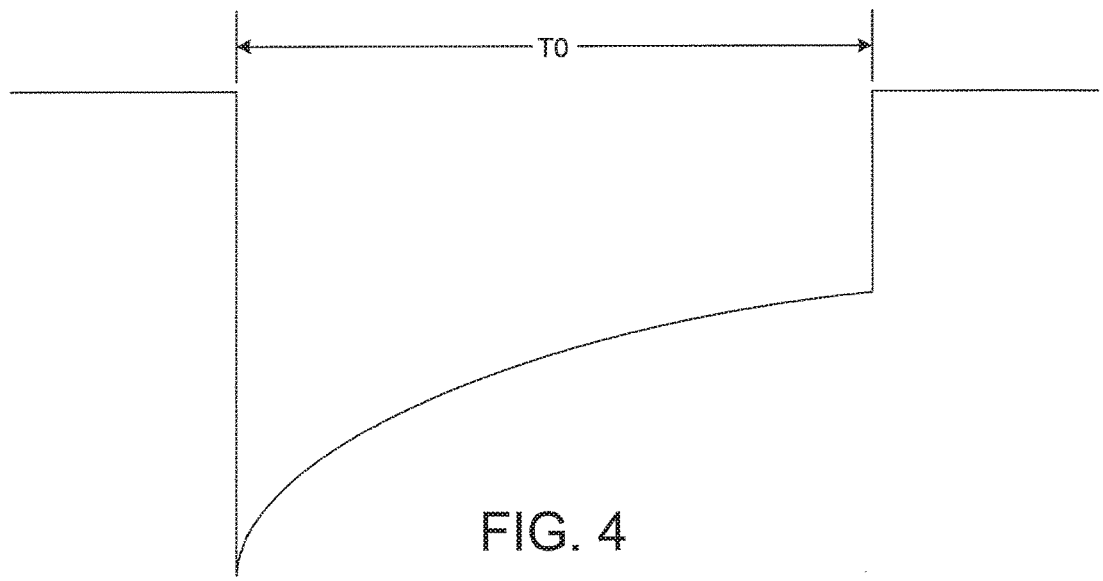
FIG. 4 is a time waveform graph illustrating a conventional pacing pulse.

Referring to FIG. 4, a typical output-pulse waveform for a conventional pacemaker is shown. The approximately-exponential decay is due to discharge of a capacitor in the pacemaker through the approximately-resistive load presented by the electrodes and leads. Typically the generator output is capacitor-coupled to one electrode to ensure net charge balance. The pulse duration is shown as T0 and is typically 500 microseconds.

When the depicted leadless pacemaker 102 is used in combination with at least one other pacemaker or other pulse generator in the cardiac pacing system 100 and is generating a pacing pulse but is not optionally sending data for communication, the pacing waveform of the leadless pacemaker 102 can also resemble the conventional pacing pulse shown in FIG. 4.

Figure 5:
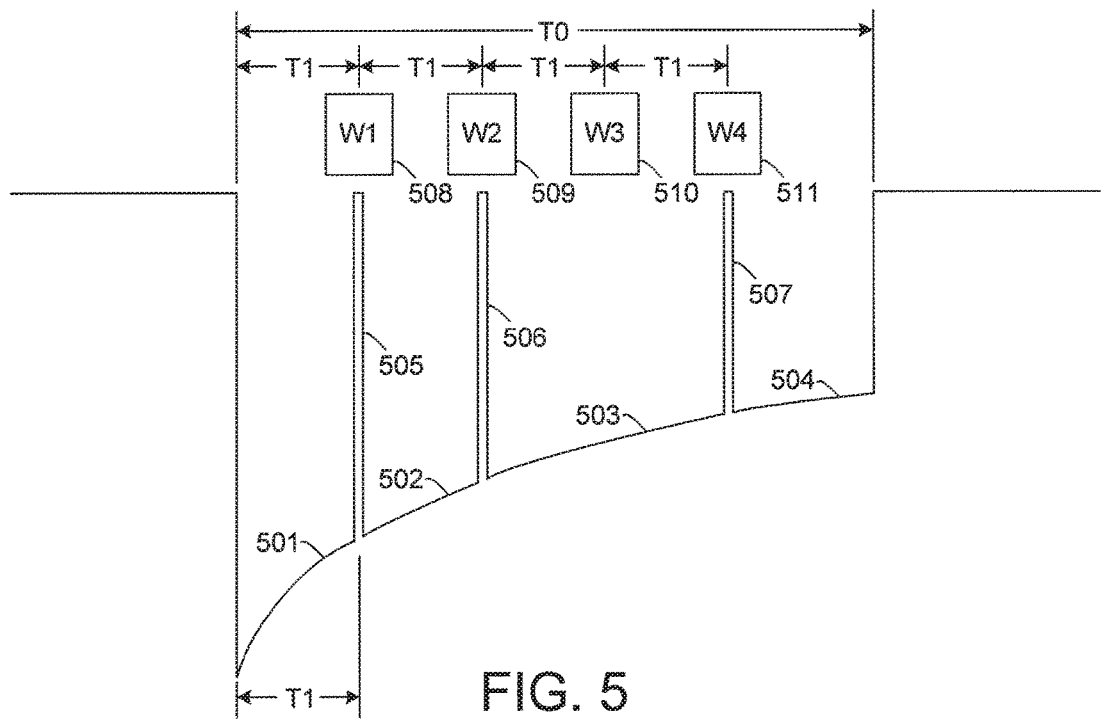
FIG. 5 is a time waveform graph depicting a pacing pulse adapted for communication as implemented for an embodiment of the illustrative pacing system.

Referring to FIG. 5, a time waveform graph depicts an embodiment of an output-pacing pulse waveform adapted for communication. The output-pulse waveform of the illustrative leadless pacemaker 102 is shown during a time when the pacemaker 102 is optionally sending data for communication and also delivering a pacing pulse, using the same pulse generator 116 and electrodes 108 for both functions.

FIG. 5 shows that the pulse generator 102 has divided the output pulse into shorter pulses 501, 502, 503, 504; separated by notches 505, 506, and 507. The pulse generator 102 times the notches 505, 506, and 507 to fall in timing windows W1, W2, and W4 designated 508, 509, and 511 respectively. Note that the pacemaker 102 does not form a notch in timing window W3 designated 510. The timing windows are each shown separated by a time T1, approximately 100 microseconds in the example.

As controlled by processor 112, pulse generator 116 selectively generates or does not generate a notch in each timing window 508, 509, 510, and 511 so that the device 102 encodes four bits of information in the pacing pulse. A similar scheme with more timing windows can send more or fewer bits per pacing pulse. The width of the notches is small, for example approximately 15 microseconds, so that the delivered charge and overall pulse width, specifically the sum of the widths of the shorter pulses, in the pacing pulse is substantially unchanged from that shown in FIG. 4. Accordingly, the pulse shown in FIG. 5 can have approximately the same pacing effectiveness as that shown in FIG. 4, according to the law of Lapique which is well known in the art of electrical stimulation.

In a leadless cardiac pacemaker, a technique can be used to conserve power when detecting information carried on pacing pulses from other implanted devices. The leadless cardiac pacemaker can have a receiving amplifier that implements multiple gain settings and uses a low-gain setting for normal operation. The low-gain setting could be insufficiently sensitive to decode gated information on a pacing pulse accurately but could detect whether the pacing pulse is present. If an edge of a pacing pulse is detected during low-gain operation, the amplifier can be switched quickly to the high-gain setting, enabling the detailed encoded data to be detected and decoded accurately. Once the pacing pulse has ended, the receiving amplifier can be set back to the low-gain setting. For usage in the decoding operation, the receiving amplifier is configured to shift to the more accurate high-gain setting quickly when activated. Encoded data can be placed at the end of the pacing pulse to allow a maximum amount of time to invoke the high-gain setting.

Figure 6:
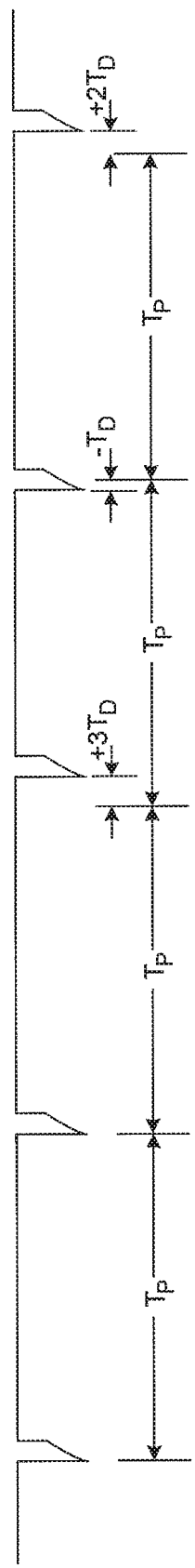
FIG. 6 is a time waveform graph showing a sample pulse waveform using off-time variation for communication.

As an alternative or in addition to using notches in the stimulation pulse, the pulses can be generated with varying off-times, specifically times between pulses during which no stimulation occurs. The variation of off-times can be small, for example less than 10 milliseconds total, and can impart information based on the difference between a specific pulse's off-time and a preprogrammed off-time based on desired heart rate. For example, the device can impart four bits of information with each pulse by defining 16 off-times centered around the preprogrammed off-time. FIG. 6 is a graph showing a sample pulse generator output which incorporates a varying off-time scheme. In the figure, time $T_P$ represents the preprogrammed pulse timing. Time $T_d$ is the delta time associated with a single bit resolution for the data sent by the pulse generator. The number of $T_d$ time increments before or after the moment specified by $T_P$ gives the specific data element transmitted. The receiver of the pulse generator's communication has advance information of the time $T_P$. The communication scheme is primarily applicable to overdrive pacing in which time $T_P$ is not dynamically changing or altered based on detected beats.

FIG. 5 depicts a technique in which information is encoded in notches in the pacing pulse. FIG. 6 shows a technique of conveying information by modulating the off-time between pacing pulses. Alternatively or in addition to the two illustrative coding schemes, overall pacing pulse width can be used to impart information. For example, a paced atrial beat may exhibit a pulse width of 500 microseconds and an intrinsic atrial contraction can be identified by reducing the pulse width by 30 microseconds. Information can be encoded by the absolute pacing pulse width or relative shift in pulse width. Variations in pacing pulse width can be relatively small and have no impact on pacing effectiveness.

In some embodiments, a pacemaker 102 can use the leadless electrodes 108 to communicate bidirectionally among multiple leadless cardiac pacemakers and transmit data including designated codes for events detected or created by an individual pacemaker wherein the codes encode information using pacing pulse width.

To ensure the leadless cardiac pacemaker functions correctly, a specific minimum internal supply voltage is maintained. When pacing tank capacitor charging occurs, the supply voltage can drop from a pre-charging level which can become more significant when the battery nears an end-of-life condition and has reduced current sourcing capability. Therefore, a leadless cardiac pacemaker can be constructed with a capability to stop charging the pacing tank capacitor when the supply voltage drops below a specified level. When charging ceases, the supply voltage returns to the value prior to the beginning of tank capacitor charging.

In another technique, the charge current can be lowered to prevent the supply voltage from dropping below the specified level. However, lowering the charge current can create difficulty in ensuring pacing rate or pacing pulse amplitude are maintained, since the lower charge current can extend the time for the pacing tank capacitor to reach a target voltage level.

The illustrative scheme for transmitting data does not significantly increase the current consumption of the pacemaker. For example, the pacemaker could transmit data continuously in a loop, with no consumption penalty.

The illustrative schemes for transmitting data enable assignment of designated codes to events detected or caused by a leadless cardiac pacemaker, such as sensing a heartbeat or delivering a pacing pulse at the location of the pacemaker that senses the event. Individual leadless cardiac pacemakers 102 in a system 100 can be configured, either at manufacture or with instructions from an external programmer or from the co-implanted ICD 106 as described hereinabove, to issue a unique code corresponding to the type of event and location of the leadless cardiac pacemaker. By delivery of a coded pacing pulse with a code assigned according to the pacemaker location, a leadless cardiac pacemaker can transmit a message to any and all other leadless cardiac pacemakers 102 and the ICD 106 implanted in the same patient, where the code signifies the origin of the event. Each other leadless cardiac pacemaker can react appropriately to the conveyed information in a predetermined manner encoded in the internal processor 112, as a function of the type and location of the event coded in the received pulse. The ICD 106 can also use the information for arrhythmia detection. A leadless cardiac pacemaker 102 can thus communicate to any and all other co-implanted leadless cardiac pacemakers and to the co-implanted ICD 106 the occurrence of a sensed heartbeat at the originating pacemaker's location by generating a coded pacing pulse triggered by the sensed event. Triggered pacing occurs in the natural refractory period following the heartbeat and therefore has no effect on the chamber where the leadless cardiac pacemaker is located.

Referring again to FIG. 1B, the circuit 132 for receiving communication via electrodes 108 receives the triggering information as described and can also optionally receive other communication information, either from the other implanted pulse generator 106 or from a programmer outside the body. This other communication could be coded with a pulse-position scheme as described in FIG. 5 or could otherwise be a pulse-modulated or frequency-modulated carrier signal, preferably from 10 kHz to 100 kHz. The illustrative scheme of a modulated carrier is applicable not only to intercommunication among multiple implanted pacemakers but also is applicable to communication from an external programmer or the co-implanted ICD 106.

The illustrative leadless pacemaker 102 could otherwise receive triggering information from the other pulse generator 106 implanted within the body via a pulse-modulated or frequency-modulated carrier signal, instead of via the pacing pulses of the other pulse generator 106.

With regard to operating power requirements in the leadless cardiac pacemaker 102, for purposes of analysis, a pacing pulse of 5 volts and 5 milliamps amplitude with duration of 500 microseconds and a period of 500 milliseconds has a power requirement of 25 microwatts.

In an example embodiment of the leadless pacemaker 102, the processor 112 typically includes a timer with a slow clock that times a period of approximately 10 milliseconds and an instruction-execution clock that times a period of approximately 1 microsecond. The processor 112 typically operates the instruction-execution clock only briefly in response to events originating with the timer, communication amplifier 134, or cardiac sensing amplifier 132. At other times, only the slow clock and timer operate so that the power requirement of the processor 112 is no more than 5 microwatts.

For a pacemaker that operates with the aforementioned slow clock, the instantaneous power consumption specification, even for a commercially-available micropower microprocessor, would exceed the battery's power capabilities and would require an additional filter capacitor across the battery to prevent a drop of battery voltage below the voltage necessary to operate the circuit. The filter capacitor would add avoidable cost, volume, and potentially lower reliability.

For example, a microprocessor consuming only 100 microamps would require a filter capacitor of 5 microfarads to maintain a voltage drop of less than 0.1 volt, even if the processor operates for only 5 milliseconds. To avoid the necessity for such a filter capacitor, an illustrative embodiment of a processor can operate from a lower frequency clock to avoid the high instantaneous power consumption, or the processor can be implemented using dedicated hardware state machines to supply a lower instantaneous peak power specification.

In a pacemaker, the cardiac sensing amplifier typically operates with no more than 5 microwatts. A communication amplifier at 100 kHz operates with no more than 25 microwatts. The battery ammeter and battery voltmeter operate with no more than 1 microwatt each.

A pulse generator typically includes an independent rate limiter with a power consumption of no more than 2 microwatts.

The total power consumption of the pacemaker is thus 64 microwatts, less than the disclosed 70-microwatt battery output.

Improvement attained by the illustrative cardiac pacing system 100 and leadless cardiac pacemaker 102 is apparent.

In a specific embodiment, the outgoing communication power requirement plus the pacing power requirement does not exceed approximately 25 microwatts. In other words, outgoing communication adds essentially no power to the power used for pacing.

The illustrative leadless cardiac pacemaker 102 can have sensing and processing circuitry that consumes no more than 10 microwatts as in conventional pacemakers.

The described leadless cardiac pacemaker 102 can have an incoming communication amplifier for receiving triggering signals and optionally other communication which consumes no more than 25 microwatts.

Furthermore, the leadless cardiac pacemaker 102 can have a primary battery that exhibits an energy density of at least 3 watt-hours per cubic centimeter (Wh/cc).

In an illustrative application of the cardiac pacing system 100, one or more leadless cardiac pacemakers 102 can be co-implanted with an ICD 106 in a single patient to provide a system for single-chamber pacing, dual-chamber pacing, CRT-D, or any other multi-chamber pacing application. Each leadless cardiac pacemaker in the system can use the illustrative communication structures to communicate the occurrence of a sensed heartbeat or a delivered pacing pulse at the location of sensing or delivery, and a communication code can be assigned to each combination of event type and location. Each leadless cardiac pacemaker can receive the transmitted information, and the code of the information can signify that a paced or sensed event has occurred at another location and indicate the location of occurrence. The receiving leadless cardiac pacemaker's processor 112 can decode the information and respond appropriately, depending on the location of the receiving pacemaker and the desired function of the system.

The implanted cardioverter-defibrillator (ICD) 106 can comprise a case and be fitted with a pair of electrodes mounted on or near the case. The ICD 106 can be configured to receive and transmit conducted communication using a pulse modulated or frequency modulated carrier signal whereby the ICD 106 can detect communication pulses from co-implanted leadless cardiac pacemakers 102 and transmit programming information to the co-implanted leadless cardiac pacemakers 102. In some embodiments, an implanted cardioverter-defibrillator (ICD) 106 configured to receive conducted communication using two implantable electrodes.

Figure 7:
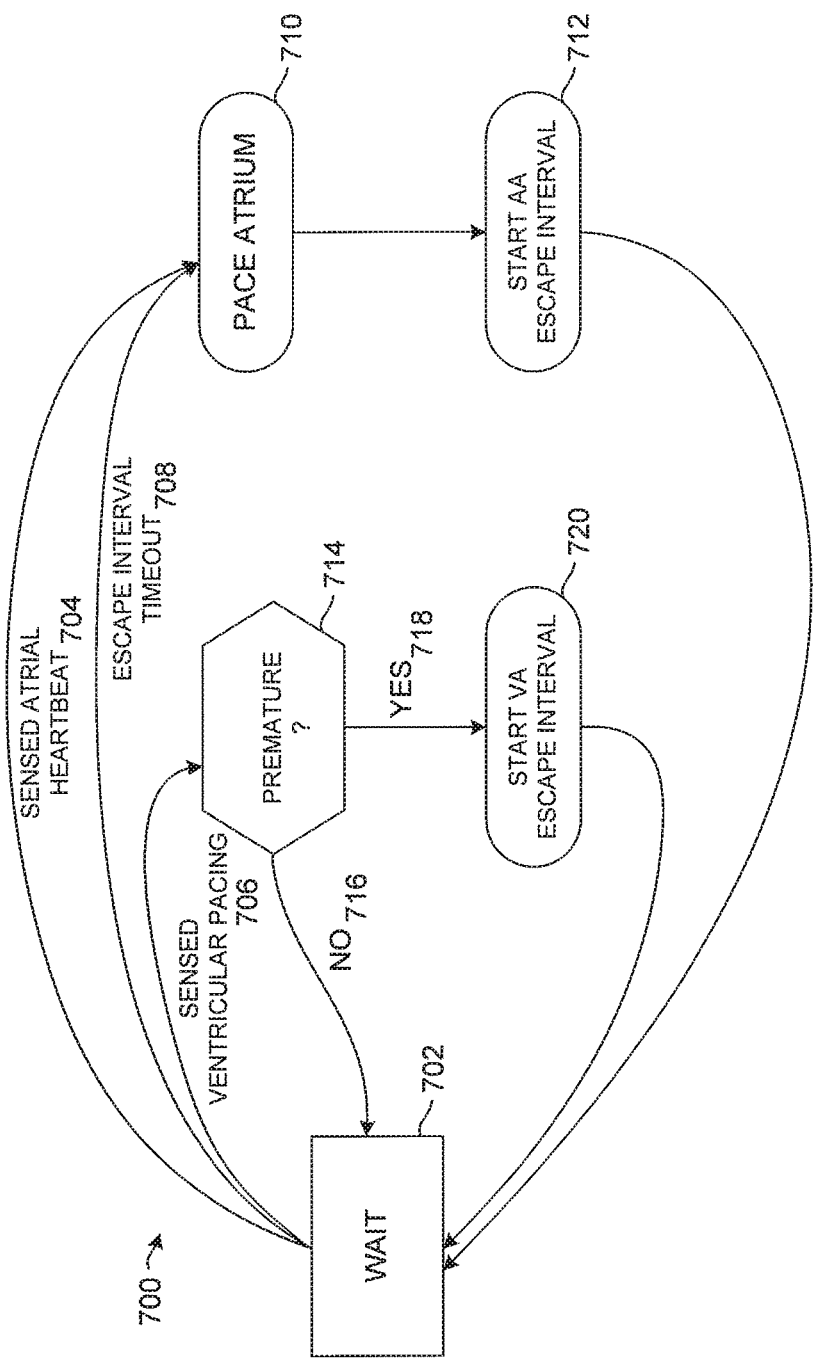
FIG. 7 is a state-mechanical representation illustrating an embodiment of a technique for operation of an atrial leadless cardiac pacemaker in a multi-chamber cardiac pacing system.
Figure 8:
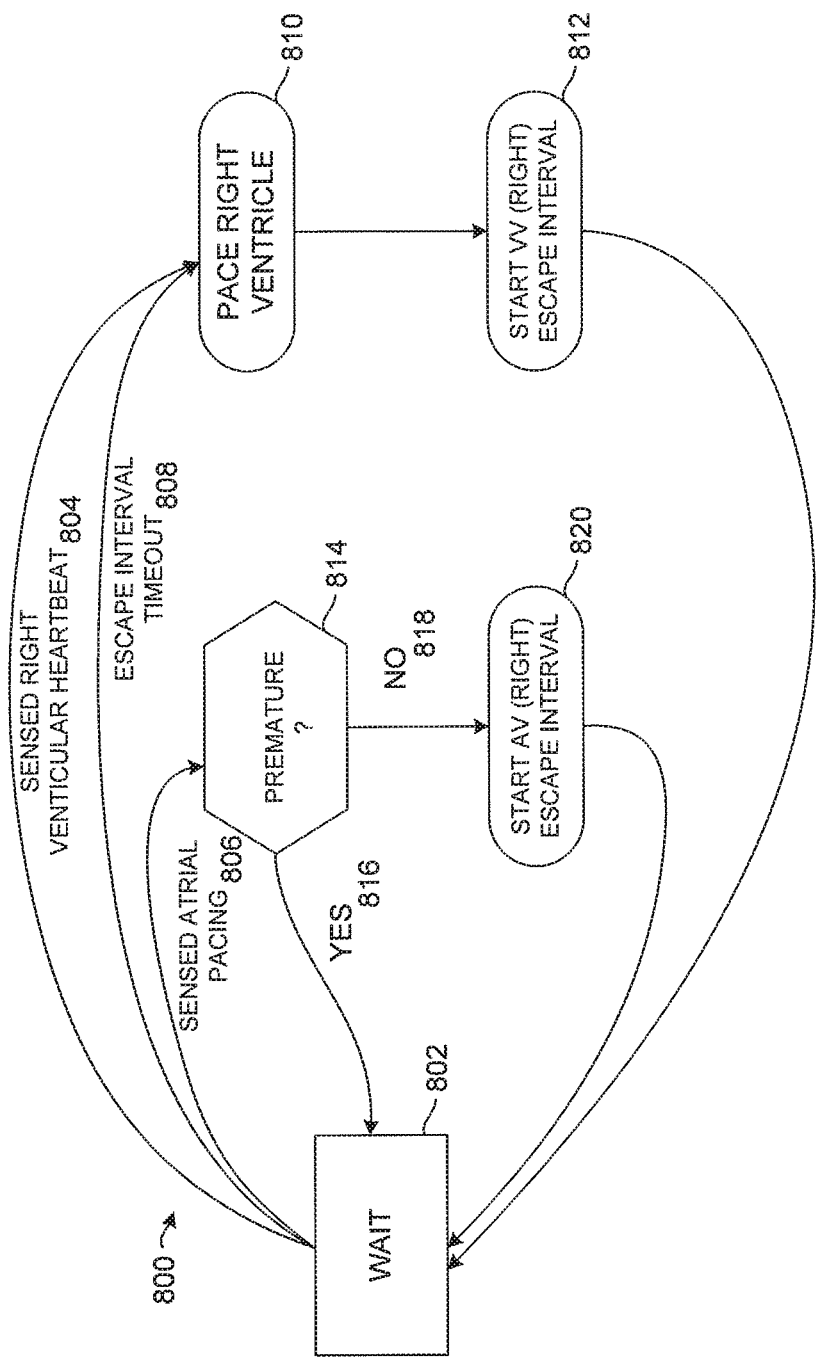
FIG. 8 is a state-mechanical representation illustrating an embodiment of a technique for operation of a right-ventricular leadless cardiac pacemaker in a multi-chamber cardiac pacing system.
Figure 9:
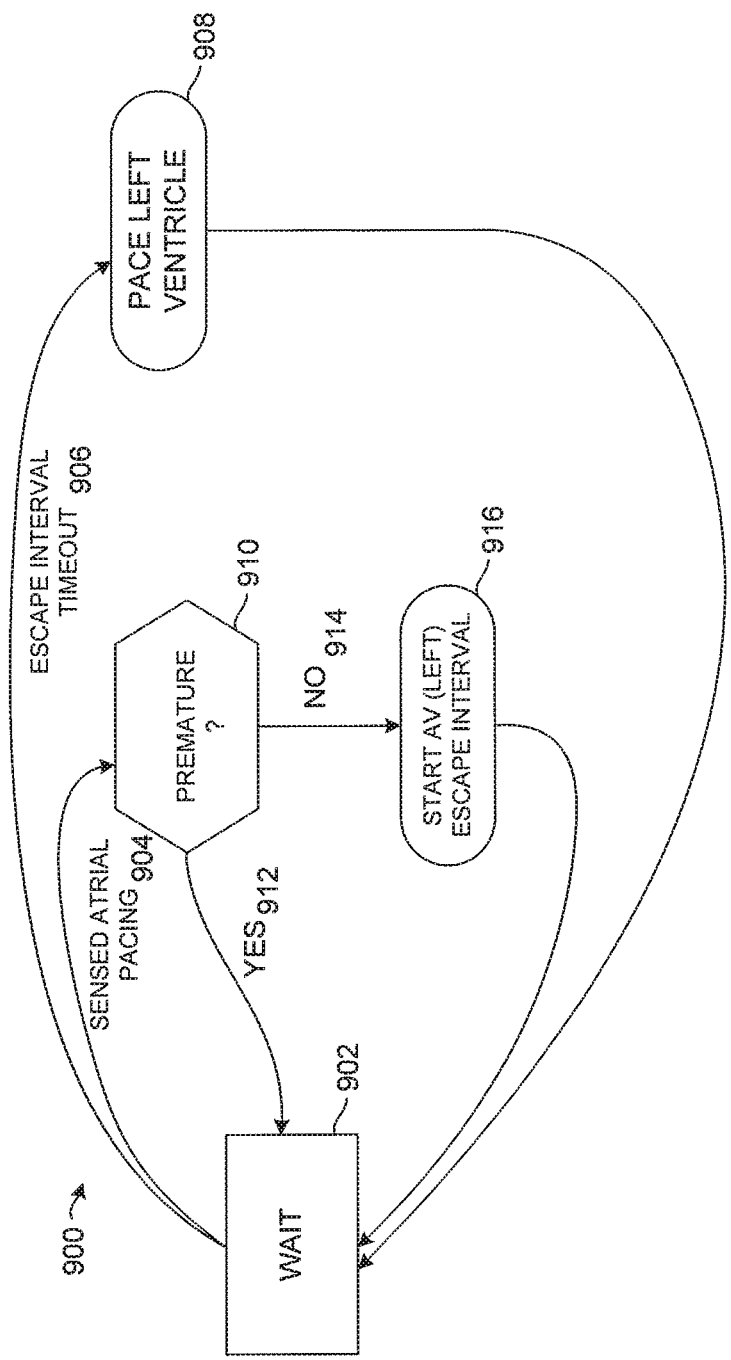
FIG. 9 is a state-mechanical representation illustrating an embodiment of a technique for operation of a left-ventricular leadless cardiac pacemaker in a multi-chamber cardiac pacing system.

FIGS. 7 and 8 are state diagrams that illustrate application of illustrative combined control operations in an atrial and right-ventricular leadless cardiac pacemaker respectively, to implement a simple dual-chamber pacing system when co-implanted with an ICD 106. FIG. 9 is a state diagram that illustrates inclusion of a left-ventricular leadless cardiac pacemaker to form a CRT-D system. In various embodiments, each leadless cardiac pacemaker may also broadcast other information destined for co-implanted leadless cardiac pacemakers and the co-implanted ICD, besides markers of paced or sensed events.

For clarity of illustration, descriptions of the atrial, right ventricular, and left-ventricular leadless cardiac pacemakers in respective FIGS. 7, 8, and 9 show only basic functions of each pacemaker. Other functions such as refractory periods, fallback mode switching, algorithms to prevent pacemaker-mediated tachycardia, and the like, can be added to the leadless cardiac pacemakers and to the system in combination. Also for clarity, functions for communication with an external programmer are not shown and are shown elsewhere herein.

Referring to FIG. 7, a state-mechanical representation shows operation of a leadless cardiac pacemaker for implantation adjacent to atrial cardiac muscle. As explained above, a leadless cardiac pacemaker can be configured for operation in a particular location and system either at manufacture or by an external programmer. Similarly, all individual pacemakers of the multiple pacemaker system can be configured for operation in a particular location and a particular functionality at manufacture and/or at programming by an external programmer wherein "configuring" means defining logic such as a state machine and pulse codes used by the leadless cardiac pacemaker.

In a cardiac pacing system, the multiple leadless cardiac pacemakers can comprise an atrial leadless cardiac pacemaker implanted in electrical contact to an atrial cardiac chamber. The atrial leadless cardiac pacemaker can be configured or programmed to perform several control operations 700 in combination with one or more other pacemakers. In a wait state 702 the atrial leadless cardiac pacemaker waits for an earliest occurring event of multiple events including a sensed atrial heartbeat 704, a communication of an event sensed on the at least two leadless electrodes encoding a pacing pulse marking a heartbeat 706 at a ventricular leadless cardiac pacemaker, or timeout of an interval timed locally in the atrial leadless cardiac pacemaker shown as escape interval timeout 708. The atrial pacemaker responds to a sensed atrial heartbeat 704 by generating 710 an atrial pacing pulse that signals to one or more other pacemakers and optionally to the co-implanted ICD that an atrial heartbeat has occurred, encoding the atrial pacing pulse with a code signifying an atrial location and a sensed event type. The atrial pacing pulse can be encoded using the technique shown in FIG. 5 with a unique code signifying the location in the atrium. After pacing the atrium, the atrial cardiac pacemaker times 712 a predetermined atrial-to-atrial (AA) escape interval. Accordingly, the atrial leadless cardiac pacemaker restarts timing 712 for a predetermined escape interval, called the AA (atrial to atrial) escape interval, which is the time until the next atrial pacing pulse if no other event intervenes. The atrial leadless cardiac pacemaker then re-enters the Wait state 702. The atrial pacemaker also responds to timeout of a first occurring escape interval 708 by delivering an atrial pacing pulse 710, causing an atrial heartbeat with the atrial pacing pulse encoding paced type and atrial location of an atrial heartbeat event. When the atrial escape interval times out, shown as transition 708, the atrial leadless cardiac pacemaker delivers an atrial pacing pulse. Because no other atrial heartbeat has occurred during the duration of the escape interval, the atrial pacing pulse does not fall in the atria's natural refractory period and therefore should effectively pace the atrium, causing an atrial heartbeat. The atrial pacing pulse, coded in the manner shown in FIG. 5, also signals to any and all other co-implanted leadless cardiac pacemakers and optionally to the co-implanted ICD that an atrial heartbeat has occurred. If functionality is enhanced for a more complex system, the atrial leadless cardiac pacemaker can use a different code to signify synchronous pacing triggered by an atrial sensed event in comparison to the code used to signify atrial pacing at the end of an escape interval. However, in the simple example shown in FIGS. 7 and 8, the same code can be used for all atrial pacing pulses. In fact, for the simple dual-chamber pacing system described in FIGS. 7 and 8 encoding may be omitted because each leadless cardiac pacemaker can conclude that any detected pacing pulse, which is not generated locally, must have originated with the other co-implanted leadless cardiac pacemaker. After generating the atrial pacing pulse 710, the atrial leadless cardiac pacemaker starts timing an atrial (AA) escape interval at action 712, and then returns to the wait state 702.

The atrial leadless cardiac pacemaker can further operate in response to another pacemaker. The atrial pacemaker can detect 706 a signal originating from a co-implanted ventricular leadless cardiac pacemaker. The atrial pacemaker can examine the elapsed amount of the atrial-to-atrial (AA) escape time interval since a most recent atrial heartbeat and determine 714 whether the signal originating from the co-implanted ventricular leadless cardiac pacemaker is premature. Thus, if the atrial leadless cardiac pacemaker detects a signal originating from a co-implanted ventricular leadless cardiac pacemaker, shown as sensed ventricular pacing 706, then the atrial device examines the amount of the escape interval elapsed since the last atrial heartbeat at decision point 714 to determine whether the ventricular event is "premature", meaning too late to be physiologically associated with the last atrial heartbeat and in effect premature with respect to the next atrial heartbeat. In the absence 716 of a premature signal, the atrial pacemaker waits 702 for an event with no effect on atrial pacing. In contrast if the signal is premature 718, the pacemaker restarts 720 a ventricle-to-atrium (VA) escape interval that is shorter than the atrial-to-atrial (AA) escape interval and is representative of a typical time from a ventricular beat to a next atrial beat in sinus rhythm, specifically the atrial interval minus the atrio-ventricular conduction time. After starting 720 the VA interval, the atrial leadless cardiac pacemaker returns to wait state 702, whereby a ventricular premature beat can be said to "recycle" the atrial pacemaker. The pacemaker responds to timeout of the atrial-to-atrial (AA) escape interval 708 by delivering an atrial pacing pulse 710, causing an atrial heartbeat. The atrial pacing pulse encodes the paced type and atrial location of an atrial heartbeat event.

The atrial leadless cardiac pacemaker can be further configured to time a prolonged post-ventricular atrial refractory period (PVARP) after recycling in presence of the premature signal, thereby preventing pacemaker-mediated tachycardia (PMT). Otherwise, if a received ventricular pacing signal evaluated at decision point 714 is not found to be premature, then the atrial leadless cardiac pacemaker follows transition 716 and re-enters the wait state 702 without recycling, thus without any effect on the timing of the next atrial pacing pulse.

Referring to FIG. 8, a state-mechanical representation depicts operation of a leadless cardiac pacemaker for implantation adjacent to right-ventricular cardiac muscle. The leadless cardiac pacemaker can be configured for operation in a particular location and system either at manufacture or by an external programmer. A system comprising multiple leadless cardiac pacemakers can include a right-ventricular leadless cardiac pacemaker implanted in electrical contact to a right-ventricular cardiac chamber. The right-ventricular leadless cardiac pacemaker can be configured to perform actions 800 for coordinated pacing in combination with the other pacemakers. The right-ventricular leadless cardiac pacemaker waits 802 for the earliest occurring event of multiple events including a sensed right-ventricular heartbeat 804, a sensed communication of a pacing pulse 806 marking a heartbeat at an atrial leadless cardiac pacemaker, and timeout 808 of an escape interval. Generally, the sensed communication of a pacing pulse 806 can be any suitable sensed communication of an event originating at another co-implanted leadless cardiac pacemaker, in the illustrative embodiment a pacing pulse marking a heartbeat at an atrial leadless cardiac pacemaker shown as sensed atrial pacing.

The escape interval timeout 808 can be any suitable timeout of an interval timed locally in the right-ventricular leadless cardiac pacemaker.

The right-ventricular leadless cardiac pacemaker responds to the sensed right-ventricular heartbeat 804 by generating 810 a right-ventricular pacing pulse that signals to at least one other pacemaker of the multiple cardiac pacemakers and optionally to the co-implanted ICD that a right-ventricular heartbeat has occurred. Thus, when a sensed right-ventricular heartbeat occurs 804, the right-ventricular leadless cardiac pacemaker generates 810 a right-ventricular pacing pulse, not to pace the heart but rather to signal to another leadless cardiac pacemaker or pacemakers that a right-ventricular heartbeat has occurred. The right-ventricular pacing pulse can be encoded with a code signifying the right-ventricular location and a sensed event type. The right-ventricular pacing pulse is coded in the manner shown in FIG. 5 with a unique code signifying the location in the right ventricle. Upon right-ventricular pacing pulse generation 810, the right-ventricular leadless cardiac pacemaker can time 812 a predetermined right ventricular-to-right ventricular (VV) escape interval. The right-ventricular leadless cardiac pacemaker restarts 812 timing of a predetermined escape interval, called the VV (right) (right-ventricular to right-ventricular) escape interval, which is the time until the next right-ventricular pacing pulse if no other event intervenes.

The right-ventricular leadless cardiac pacemaker can further be configured to set the ventricular-to-ventricular (VV) escape interval longer than a predetermined atrial-to-atrial (AA) escape interval to enable backup ventricular pacing at a low rate corresponding to the VV escape interval in case of failure of a triggered signal from a co-implanted atrial leadless cardiac pacemaker. Typically, the VV (right) escape interval is longer than the AA interval depicted in FIG. 7, so that the system supports backup ventricular pacing at a relatively low rate in case of failure of the co-implanted atrial leadless cardiac pacemaker. In normal operation of the system, timeout of the VV interval never occurs. The right-ventricular leadless cardiac pacemaker then re-enters the Wait state 802.

The right-ventricular leadless cardiac pacemaker can respond to timeout of a first occurring escape interval 808 by delivering 810 a right ventricular pacing pulse, causing a right ventricular heartbeat. The right ventricular pacing pulse can encode information including paced type and right-ventricular location of a right ventricular heartbeat event.

When the right-ventricular escape interval times out 808, the right-ventricular leadless cardiac pacemaker delivers 810 a right-ventricular pacing pulse. Because no other right-ventricular heartbeat has occurred during the duration of the VV escape interval, the pacing pulse 810 does not fall in the ventricles' natural refractory period and therefore should effectively pace the ventricles, causing a ventricular heartbeat. The right-ventricular pacing pulse, coded in the manner shown in FIG. 5, also signals to any and all other co-implanted leadless cardiac pacemakers and optionally to the co-implanted ICD that a right-ventricular heartbeat has occurred. If useful for the function of a more complex system, the right-ventricular leadless cardiac pacemaker can use a different code to signify synchronous pacing triggered by a right-ventricular sensed event in comparison to the code used to signify right-ventricular pacing at the end of a VV escape interval. However, in the simple example shown in FIGS. 7 and 8, the same code can be used for all right-ventricular pacing pulses. In fact, for the simple dual-chamber pacing system described in FIGS. 7 and 8, a code may be omitted because each leadless cardiac pacemaker can conclude that any detected pacing pulse which is not generated local to the pacemaker originates with the other co-implanted leadless cardiac pacemaker. After generating 810 the right-ventricular pacing pulse, the right-ventricular leadless cardiac pacemaker starts timing 812 a right-ventricular escape interval VV, and then returns to the wait state 802.

The right-ventricular leadless cardiac pacemaker can further be configured to detect 806 a signal originating from a co-implanted atrial leadless cardiac pacemaker. The right-ventricular leadless cardiac pacemaker examines the elapsed amount of the ventricular-to-ventricular (VV) escape interval since a most recent right-ventricular heartbeat and determines 814 whether the signal originating from the co-implanted atrial leadless cardiac pacemaker is premature. An atrial event is defined as premature if too early to trigger an atrio-ventricular delay to produce a right-ventricular heartbeat. In the presence of a premature signal 816, the right-ventricular leadless cardiac pacemaker returns to the wait state 802 with no further action. Thus, a premature atrial beat does not affect ventricular pacing. In the absence of a premature signal 818, the right-ventricular leadless cardiac pacemaker starts 820 a right atrium to right ventricular (AV) escape interval that is representative of a typical time from an atrial beat to a right-ventricular beat in sinus rhythm. Thus a non-premature atrial event leads to starting 820 an AV (right) atrium to right-ventricular escape interval that represents a typical time from an atrial beat to a right-ventricular beat in normally-conducted sinus rhythm. After starting 820 the AV interval, the right-ventricular leadless cardiac pacemaker returns to the wait state 802 so that a non-premature atrial beat can "trigger" the right-ventricular pacemaker after a physiological delay. The right-ventricular leadless cardiac pacemaker also responds to timeout of either the VV escape interval and the AV escape interval 808 by delivering 810 a right ventricular pacing pulse, causing a right ventricular heartbeat. The right ventricular pacing pulse encodes paced type and right-ventricular location of a right ventricular heartbeat event.

Accordingly, co-implanted atrial and right-ventricular leadless cardiac pacemakers depicted in FIGS. 7 and 8 cooperate to form a dual-chamber pacing system.

Referring to FIG. 9, a state-mechanical representation illustrates the operation of a leadless cardiac pacemaker for implantation adjacent to left-ventricular cardiac muscle. The left-ventricular cardiac pacemaker can be used in combination with the dual-chamber pacemaker that includes the atrial leadless cardiac pacemaker and the right-ventricular leadless cardiac pacemaker described in FIGS. 7 and 8 respectively to form a system for CRT-D. A leadless cardiac pacemaker, for example the left-ventricular cardiac pacemaker, can be configured for operation in a particular location and system either at manufacture or by an external programmer.

A cardiac pacing system, such as a CRT-D system, can include multiple leadless cardiac pacemakers including a left-ventricular leadless cardiac pacemaker implanted in electrical contact to a left-ventricular cardiac chamber. The left-ventricular leadless cardiac pacemaker can execute operations of an illustrative pacing method 900. In a wait state 902, the left-ventricular cardiac pacemaker waits 902 at the left-ventricular leadless cardiac pacemaker for an earliest occurring event of multiple events including a sensed communication 904 of a pacing pulse marking a heartbeat at an atrial leadless cardiac pacemaker and timeout 906 of a left ventricular escape interval. Generally, the sensed communication 904 can be the sensed communication of an event originating at another co-implanted leadless cardiac pacemaker, in the illustrative embodiment a pacing pulse marking a heartbeat at an atrial leadless cardiac pacemaker shown as sensed atrial pacing. The escape interval timeout 906 can be timeout of an interval timed locally in the left-ventricular leadless cardiac pacemaker. In the wait state 902 for the left-ventricular leadless cardiac pacemaker, operation is simplified and the left-ventricular pacemaker does not respond to left-ventricular heartbeats. Also, the left-ventricular cardiac pacemaker does not pace the left ventricle in the absence of a triggering signal from the atrial leadless cardiac pacemaker. The left-ventricular cardiac pacemaker responds to timeout 906 of the left ventricular escape interval by delivering 908 a left ventricular pacing pulse, causing a left ventricular heartbeat. The left ventricular pacing pulse encodes the type and location of a left ventricular heartbeat event. The left-ventricular pacing pulse can be coded in the manner shown in FIG. 5 to communicate signals to any and all other co-implanted leadless cardiac pacemakers and optionally to the co-implanted ICD that a left-ventricular heartbeat has occurred, although such encoding is not necessary in the simplified CRT-D system shown in the described embodiment because the other leadless cardiac pacemakers do not react to left-ventricular pacing. After generating 908 the left-ventricular pacing pulse, the left-ventricular leadless cardiac pacemaker returns to the wait state 902.

The left-ventricular leadless cardiac pacemaker can be further configured detect a signal originating from a co-implanted atrial leadless cardiac pacemaker and examine the elapsed amount of the left ventricular escape interval since a most recent left-ventricular heartbeat. The left-ventricular cardiac pacemaker can determine 910 whether the signal originating from the co-implanted atrial leadless cardiac pacemaker is premature. If the left-ventricular leadless cardiac pacemaker detects sensed atrial pacing, then the left-ventricular device determines whether the atrial event is premature, meaning too early to trigger an atrio-ventricular delay to produce a left-ventricular heartbeat. In the presence of a premature signal 912, the left-ventricular cardiac pacemaker reverts to the wait state 902 and waits for an event with no effect on ventricular pacing so that a premature atrial beat does not affect ventricular pacing. In absence of a premature signal 914, the left-ventricular cardiac pacemaker starts 916 a left atrium to left ventricular (AV) escape interval that is representative of a typical time from an atrial beat to a left ventricular beat in normally-conducted sinus rhythm. As shown in the depicted embodiment, the AV (left) escape interval can have a different value from the AV (right) escape interval. After starting 916 the AV interval, the left-ventricular leadless cardiac pacemaker returns to wait state 902. Accordingly, a non-premature atrial beat can "trigger" the left-ventricular pacemaker after a physiological delay.

The left-ventricular cardiac pacemaker also responds to timeout 906 of the AV escape interval by delivering 908 a left ventricular pacing pulse, causing a left ventricular heartbeat. The left ventricular pacing pulse encodes paced type and left ventricular location of a left ventricular heartbeat event.

In various embodiments, the multiple leadless cardiac pacemakers can comprise a right ventricular leadless cardiac pacemaker and a left ventricular leadless cardiac pacemaker that are configured to operate with atrio-ventricular (AV) delays whereby a left ventricular pacing pulse can be delivered before, after, or substantially simultaneously with a right ventricular pacing pulse. For example, multiple co-implanted leadless cardiac pacemakers that function according to the state diagrams shown in FIGS. 7, 8, and 9 can support CRT-D with left-ventricular pacing delivered before, at the same time as, or after right-ventricular pacing.

The co-implanted ICD can configure the leadless cardiac pacemakers via conducted communication in a similar manner to an external programmer. In particular, the ICD can configure them to deliver overdrive anti-tachycardia pacing in response to detected tachyarrhythmias.

In various embodiments, multiple co-implanted leadless cardiac pacemakers can be configured for multi-site pacing that synchronizes depolarization for tachyarrhythmia prevention.

The illustrative system can be useful in conjunction with an ICD, and more particularly with a subcutaneous ICD, for such an ICD has no other means to provide bradycardia support, anti-tachycardia pacing, and CRT.

Referring to FIGS. 10A, 10B, 11A, 11B, 12A, and 12B, schematic flow charts illustrate an embodiment of a method for operating a cardiac pacing system that comprises an implantable cardioverter-defibrillator (ICD) and one or more leadless cardiac pacemakers configured for implantation in electrical contact with a cardiac chamber and configured for performing cardiac pacing functions in combination with the ICD. Pacing functions include delivering cardiac pacing pulses, sensing evoked and/or natural cardiac electrical signals, and bidirectionally communicating with a co-implanted ICD and/or at least one other pacemaker. The one or more leadless cardiac pacemakers are further configured to communicate a code that signifies occurrence of sensed cardiac electrical signals and/or delivered pacing pulses and identifies an event type and/or location.

Two or more electrodes are coupled to the ICD and configured to transmit and/or receive conducted communication using a pulse-modulated or frequency-modulated carrier signal. The ICD can be configured to detect communication pulses from at least one co-implanted leadless cardiac pacemaker and transmit programming information to the at least one co-implanted leadless cardiac pacemaker.

The leadless cardiac pacemakers can be configured to broadcast information to the co-implanted ICD and/or at least one other pacemaker. The leadless cardiac pacemakers can further be configured to receive the code and react based on the code, location of the receiving leadless cardiac pacemaker, and predetermined system functionality.

In various embodiments, configurations, and conditions, the leadless cardiac pacemakers can be adapted to perform one or more cardiac pacing functions such as single-chamber pacing, dual-chamber pacing, cardiac resynchronization therapy with cardioversion/defibrillation (CRT-D), single-chamber overdrive pacing for prevention of tachyarrhythmias, single-chamber overdrive pacing for conversion of tachyarrhythmias, multiple-chamber pacing for prevention of tachyarrhythmias, multiple-chamber pacing for conversion of tachyarrhythmias, and the like.

Multiple leadless cardiac pacemakers can be configured for co-implantation in a single patient and multiple-chamber pacing including CRT-D. Bidirectional communication among the multiple leadless cardiac pacemakers can be adapted to communicate notification of a sensed heartbeat or delivered pacing pulse event and encoding type and location of the event to at least one pacemaker of the leadless cardiac pacemaker plurality. The one or more pacemakers that receive the communication can decode the information and react depending on location of the receiving pacemaker and predetermined system functionality.

Figure 10A:
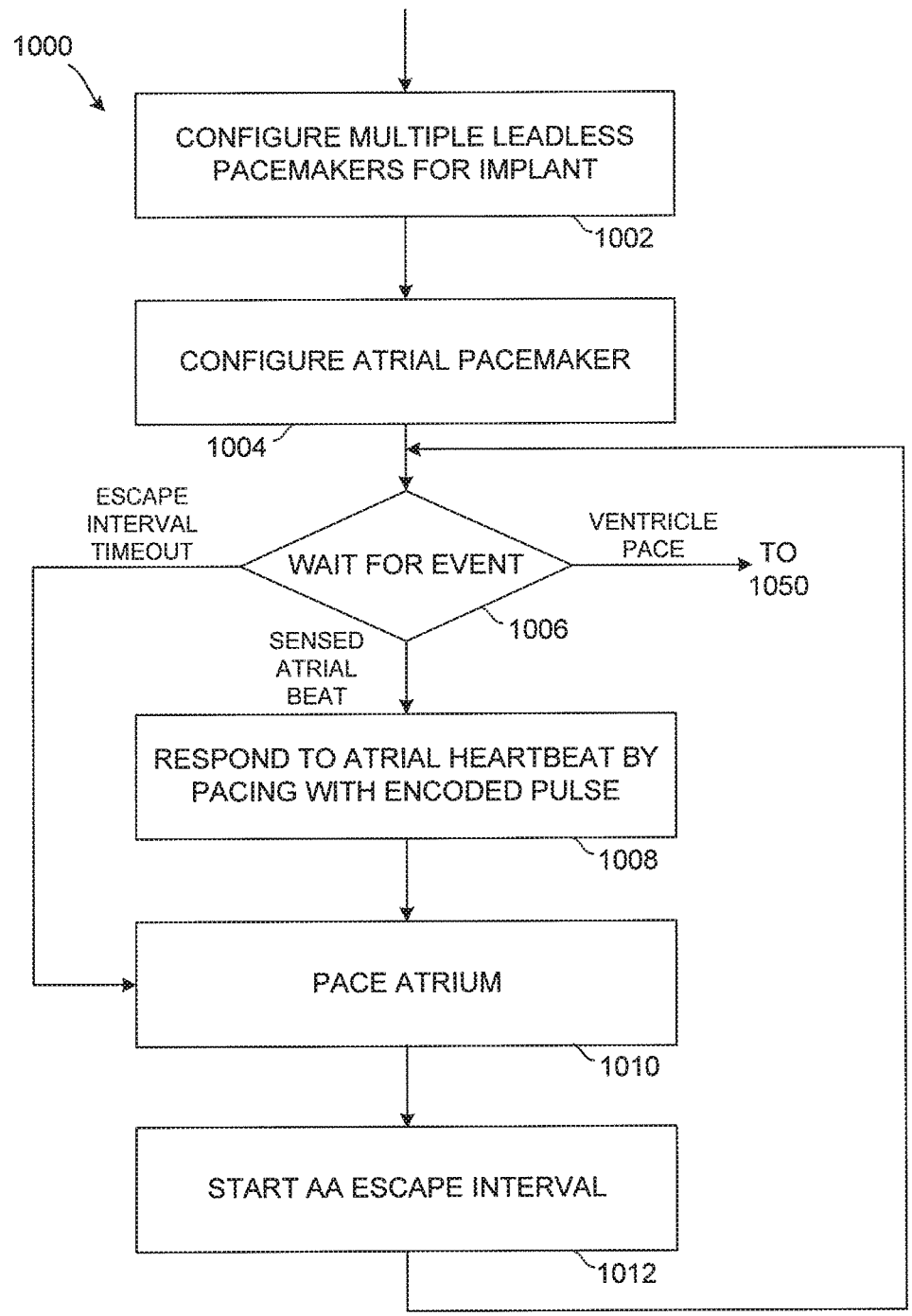
FIGS. 10A and 10B are schematic flow charts that depict embodiments of methods for operating an atrial leadless cardiac pacemaker in a cardiac pacing system including an implantable cardioverter-defibrillator (ICD) and one or more leadless cardiac pacemakers.

FIG. 10A depicts a method 1000 for operating one or more leadless cardiac pacemakers including an atrial leadless cardiac pacemaker that is implanted in electrical contact to an atrial cardiac chamber and configured for dual-chamber pacing in combination with the co-implanted ICD. Cardiac pacing comprises configuring 1002 a multiple leadless cardiac pacemakers for implantation and configuring 1004 an atrial leadless cardiac pacemaker of the multiple leadless cardiac pacemakers for implantation in electrical contact to an atrial cardiac chamber. The atrial leadless cardiac pacemaker waits 1006 for an earliest occurring event of multiple events including a sensed atrial heartbeat, a communication of an event sensed on the at least two leadless electrodes encoding a pacing pulse marking a heartbeat at a ventricular leadless cardiac pacemaker, and timeout of an atrial-to-atrial (AA) escape interval. The atrial leadless cardiac pacemaker responds 1008 to the sensed atrial heartbeat by generating an atrial pacing pulse that signals to at least one pacemaker of the multiple leadless cardiac pacemakers and optionally to the co-implanted ICD that an atrial heartbeat has occurred and that encodes the atrial pacing pulse with a code signifying an atrial location and a sensed event type. After either a sensed atrial heartbeat or timeout of an escape interval, the atrial leadless cardiac pacemaker delivers 1010 an atrial pacing pulse, causing an atrial heartbeat and starts 1012 timing a predetermined length AA escape interval, then waiting 1006 for an event. The atrial pacing pulse identifies paced type and/or atrial location of an atrial heartbeat event.

In some embodiments, the atrial leadless cardiac pacemaker can encode an atrial pacing pulse that identifies synchronous pacing triggered by an atrial sensed event with a first code and encode an atrial pacing pulse that identifies atrial pacing following the AA escape interval with a second code distinct from the first code.

The atrial leadless cardiac pacemaker can, upon delivery of an atrial pacing pulse, time an atrial-to-atrial (AA) escape interval.

Figure 10B:
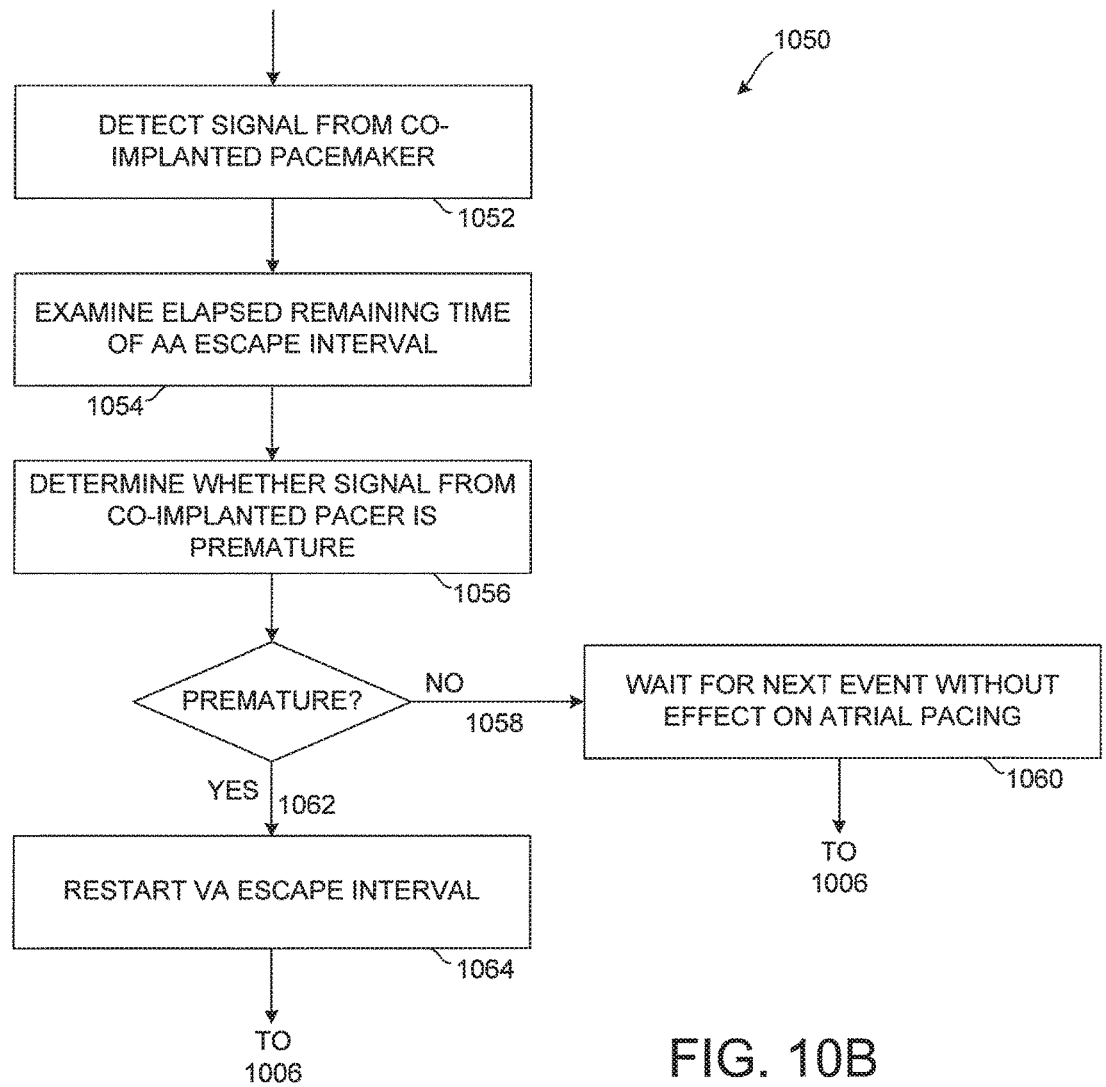

FIG. 10B is a flow chart showing another aspect 1050 of the method embodiment for operating an atrial leadless cardiac pacemaker. The atrial leadless cardiac pacemaker detects 1052 a signal originating from a co-implanted ventricular leadless cardiac pacemaker and examines 1054 an elapsed amount of the atrial-to-atrial (AA) escape interval since a most recent atrial heartbeat, determining 1056 whether the signal originating from the co-implanted ventricular leadless cardiac pacemaker is premature. In absence of a premature signal 1058, the atrial leadless cardiac pacemaker waits 1060 for an event with no effect on atrial pacing, returning to wait state 1006. In presence of a premature signal 1062, the atrial leadless cardiac pacemaker restarts 1064 a ventricle-to-atrium (VA) escape interval that is shorter than the atrial-to-atrial (AA) escape interval and representative of a typical time from a ventricular beat to a next atrial beat in sinus rhythm, then returns to wait state 1006.

Figure 11A:
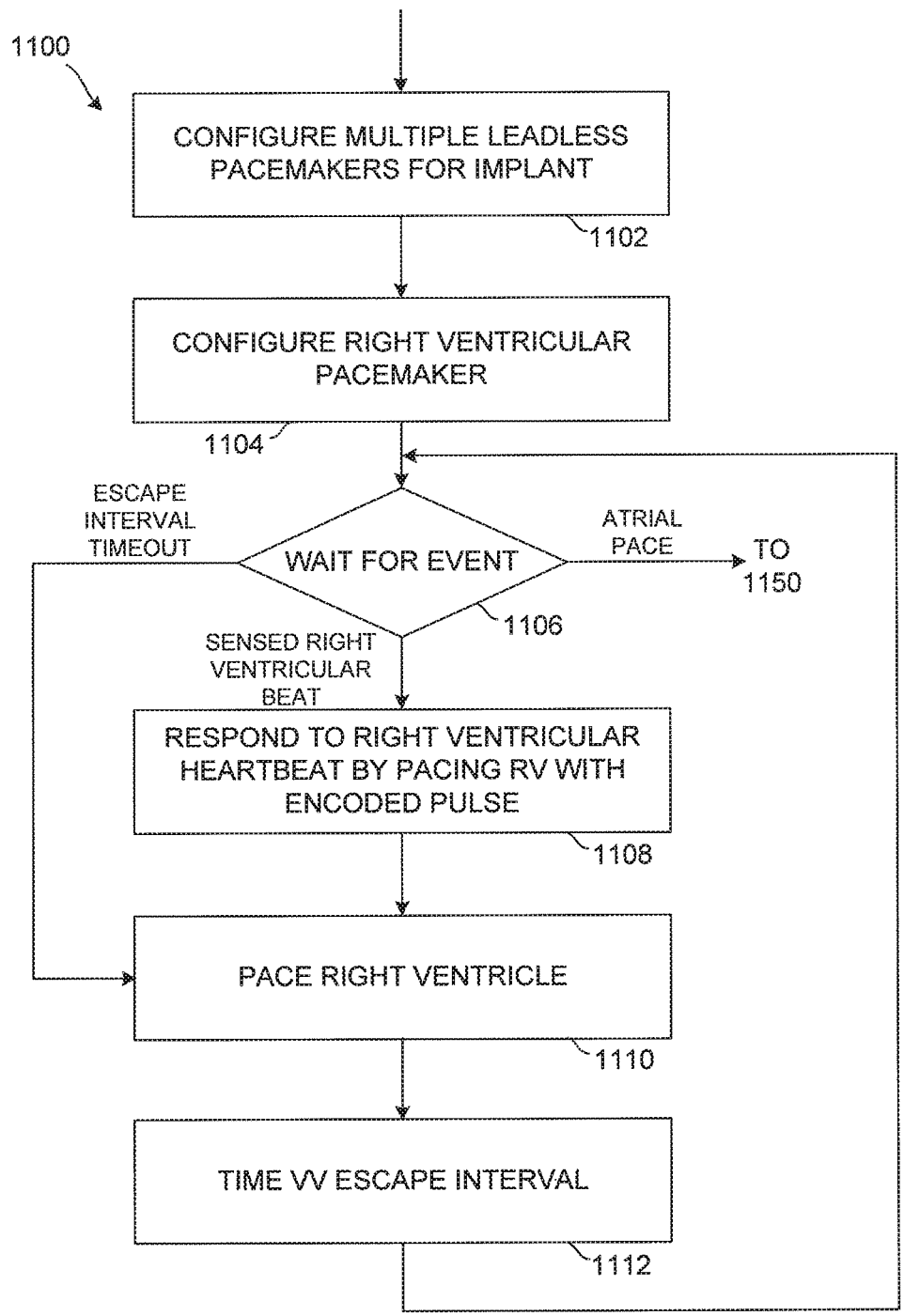
FIGS. 11A and 11B are schematic flow charts that depict embodiments of methods for operating a right-ventricular leadless cardiac pacemaker in a cardiac pacing system including an implantable cardioverter-defibrillator (ICD) and one or more leadless cardiac pacemakers.
Figure 11B:
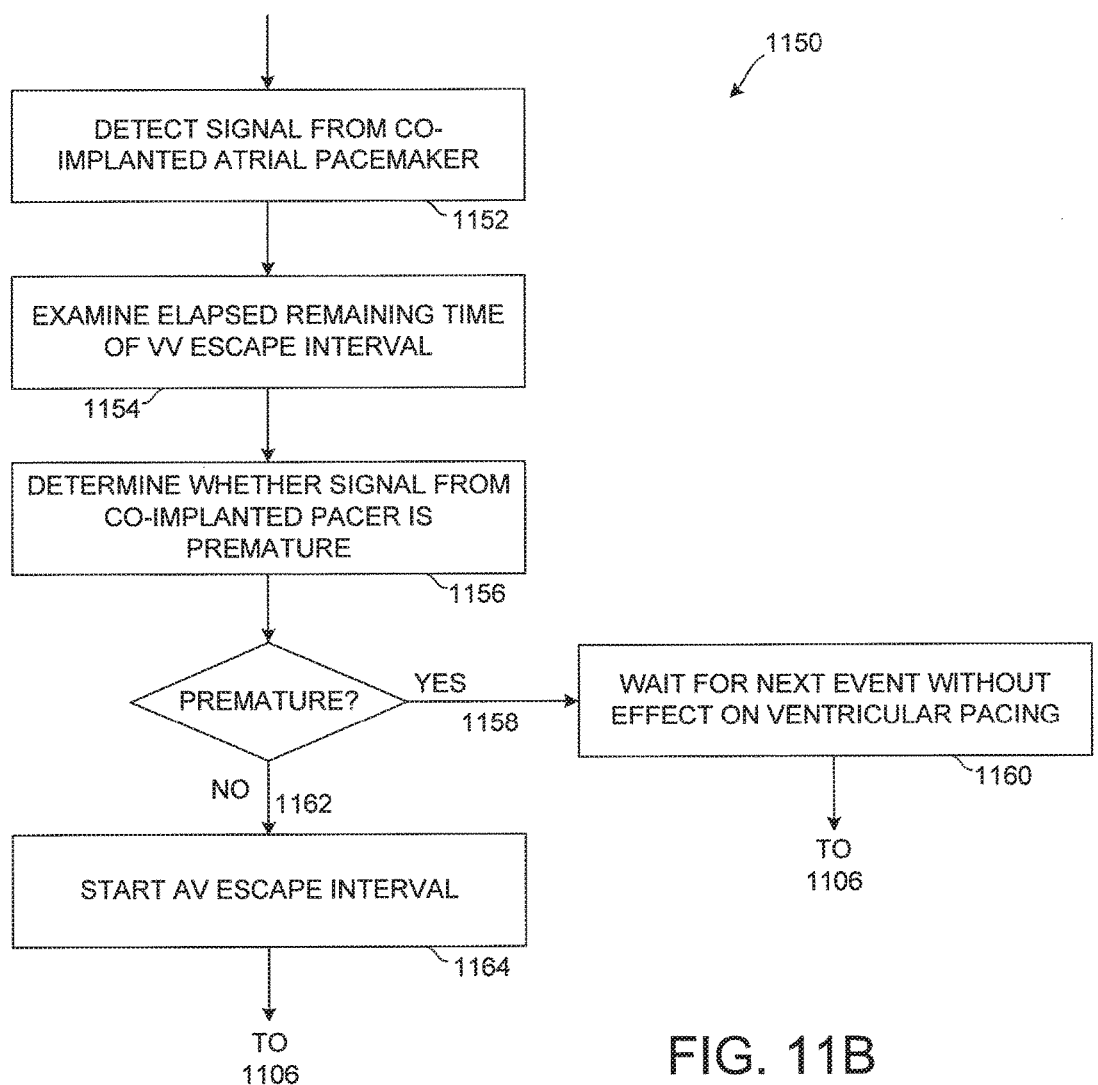

Referring to FIGS. 11A and 11B, schematic flow charts illustrate an embodiment of a method for operating a right-ventricular leadless cardiac pacemaker in an illustrative multi-chamber cardiac pacing system. The right-ventricular leadless cardiac pacemaker is implanted in electrical contact to a right-ventricular cardiac chamber and configured for dual-chamber pacing in combination with the co-implanted ICD. FIG. 11A depicts a method 1100 for cardiac pacing comprising configuring 1102 a plurality of leadless cardiac pacemakers for implantation and configuring 1104 a right-ventricular leadless cardiac pacemaker of the multiple leadless cardiac pacemakers for implantation in electrical contact to a right-ventricular cardiac chamber. The right-ventricular leadless cardiac pacemaker waits 1106 for an earliest occurring event of a several events including a sensed right-ventricular heartbeat, a sensed communication of a pacing pulse marking a heartbeat at an atrial leadless cardiac pacemaker, and timeout of an escape interval. The right-ventricular leadless cardiac pacemaker responds 1108 to the sensed right-ventricular heartbeat by generating a right-ventricular pacing pulse that signals to at least one pacemaker of the leadless cardiac pacemakers and optionally to the co-implanted ICD that a right-ventricular heartbeat has occurred and that encodes the right-ventricular pacing pulse with a code signifying a right-ventricular location and a sensed event type. The right-ventricular leadless cardiac pacemaker responds 1110 to timeout of a first-occurring escape interval by delivering a right ventricular pacing pulse, causing a right ventricular heartbeat, with the right ventricular pacing pulse encoding paced type and right ventricular location of a right ventricular heartbeat event, and times 1112 a predetermined ventricular-to-ventricular (VV) escape interval.

In some embodiments, the right-ventricular leadless cardiac pacemaker can encode a right-ventricular pacing pulse that identifies synchronous pacing triggered by a right-ventricular sensed event with a first code and encode a right-ventricular pacing pulse that identifies right-ventricular pacing following a ventricular-to-ventricular (VV) escape interval with a second code distinct from the first code.

In some embodiments, the right-ventricular leadless cardiac pacemaker, upon delivery of a right-ventricular pacing pulse, can time a ventricular-to-ventricular (VV) escape interval.

FIG. 11B is a flow chart showing another aspect of an embodiment of a method 1150 for operating a right-ventricular leadless cardiac pacemaker. The right-ventricular leadless cardiac pacemaker detects 1152 a signal originating from a co-implanted atrial leadless cardiac pacemaker, examines 1154 the elapsed amount of the ventricular-to-ventricular (VV) escape interval since a most recent right-ventricular heartbeat, and determines 1156 whether the signal originating from the co-implanted atrial leadless cardiac pacemaker is premature. In presence 1158 of a premature signal, the right-ventricular leadless cardiac pacemaker waits 1160 for an event with no effect on ventricular pacing, returning to wait state 1106. In absence 1162 of a premature signal, the right-ventricular leadless cardiac pacemaker starts 1164 a right atrium to right ventricular (AV) escape interval that is representative of a typical time from an atrial beat to a right-ventricular beat in sinus rhythm, and then returns to the wait state 1106.

Figure 12A:
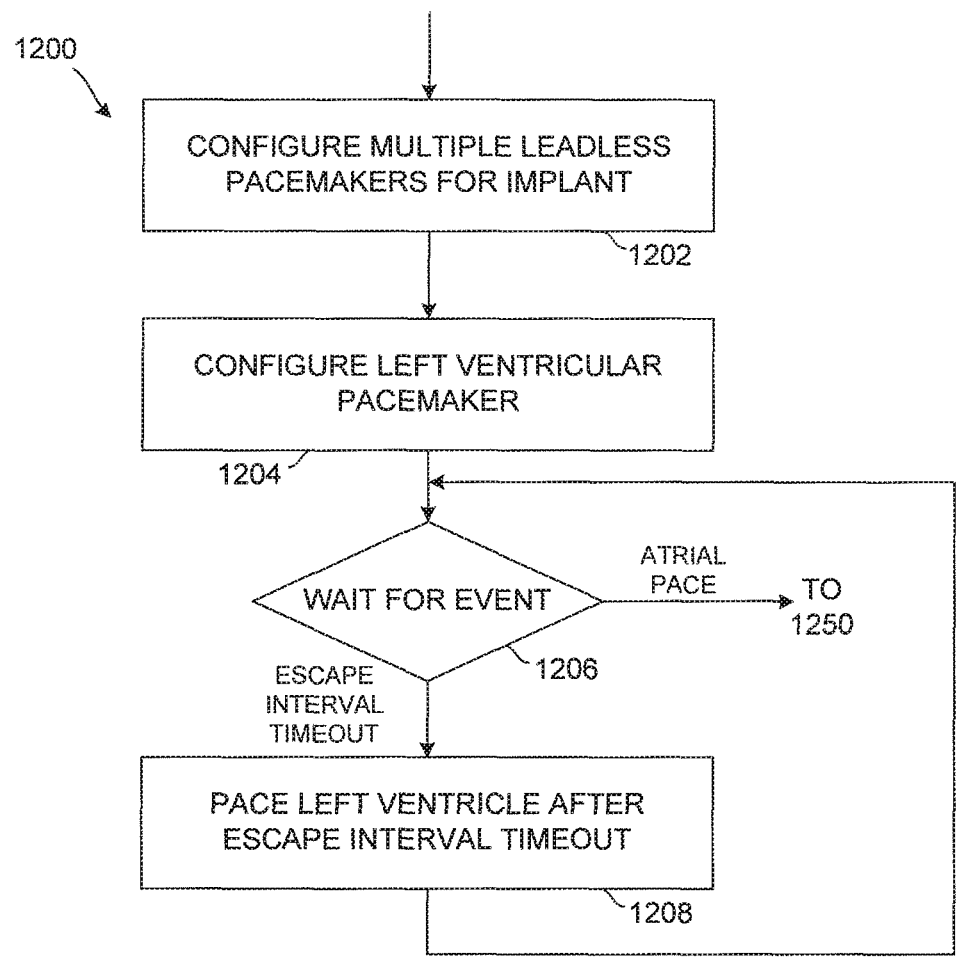
FIGS. 12A and 12B are schematic flow charts that depict embodiments of methods for operating a left-ventricular leadless cardiac pacemaker in a cardiac pacing system including an implantable cardioverter-defibrillator (ICD) and one or more leadless cardiac pacemakers.
Figure 12B:
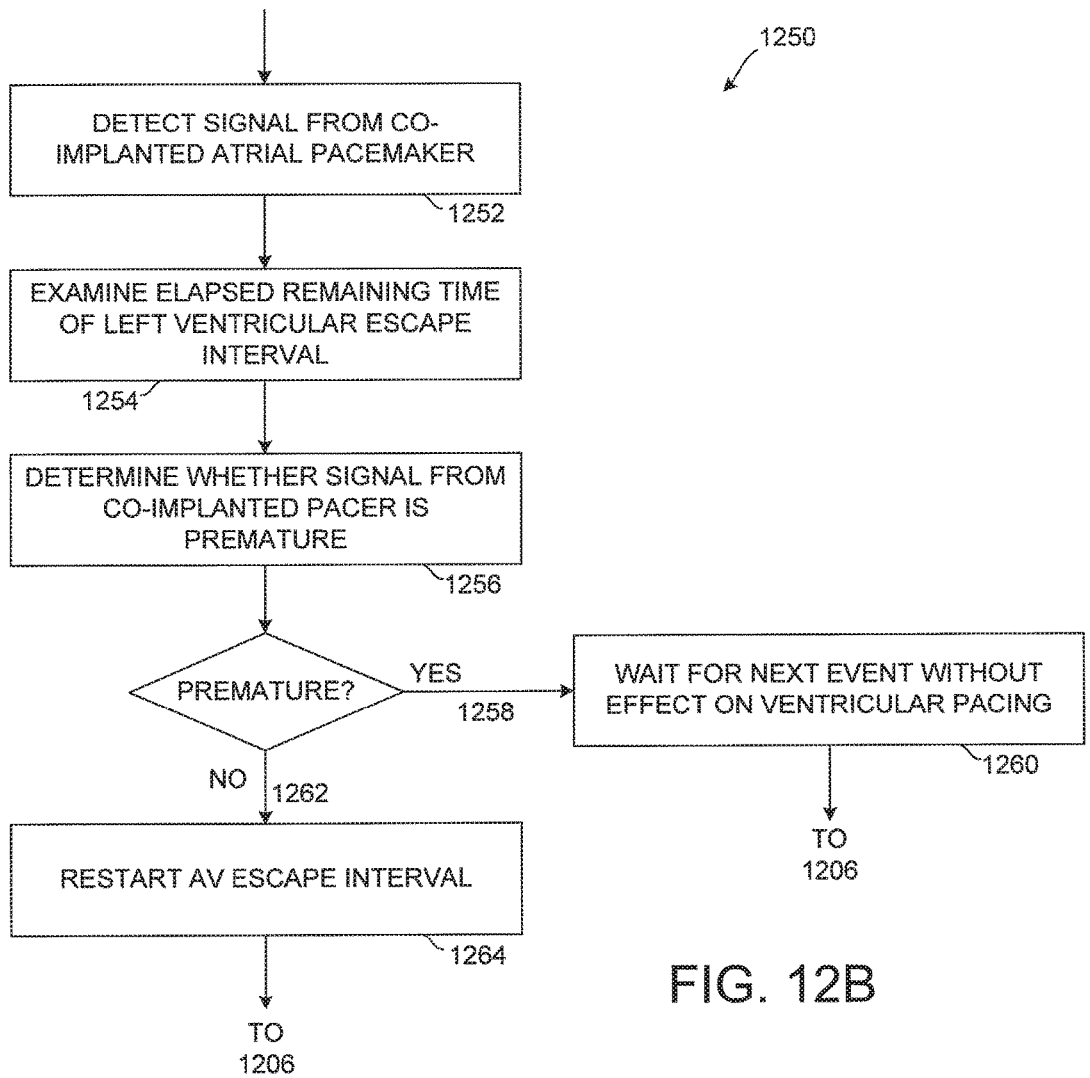

Referring to FIGS. 12A and 12B, schematic flow charts illustrate embodiments of a method for operating a left-ventricular leadless cardiac pacemaker in multi-chamber cardiac pacing system. The left-ventricular leadless cardiac pacemaker is implanted in electrical contact to a left-ventricular cardiac chamber and configured for dual-chamber pacing in combination with the co-implanted ICD. FIG. 12A depicts a method 1200 for cardiac pacing comprising configuring 1202 a plurality of leadless cardiac pacemakers for implantation and configuring 1204 a left-ventricular leadless cardiac pacemaker of the leadless cardiac pacemaker plurality for implantation in electrical contact to a left-ventricular cardiac chamber and for operation in cardiac resynchronization therapy (CRT-D). The left-ventricular cardiac pacemaker waits 1206 at the left-ventricular leadless cardiac pacemaker for an earliest occurring event of a plurality of events comprising a sensed communication of a pacing pulse marking a heartbeat at an atrial leadless cardiac pacemaker and timeout of a left ventricular escape interval. The left-ventricular cardiac pacemaker responds 1208 to timeout of the left ventricular escape interval by delivering a left ventricular pacing pulse, causing a left ventricular heartbeat, the left ventricular pacing pulse encoding type and location of a left ventricular heartbeat event.

In some embodiments, the left-ventricular cardiac pacemaker can configure the left-ventricular leadless cardiac pacemaker for operation in cardiac resynchronization therapy (CRT-D).

FIG. 12B is a flow chart showing another embodiment of a method 1250 for operating a left-ventricular leadless cardiac pacemaker. The left-ventricular leadless cardiac pacemaker detects 1252 a signal originating from a co-implanted atrial leadless cardiac pacemaker, examines 1254 the elapsed amount of the left ventricular escape interval since a most recent left-ventricular heartbeat, and determines 1256 whether the signal originating from the co-implanted atrial leadless cardiac pacemaker is premature. In the presence 1258 of a premature signal, the left-ventricular cardiac pacemaker waits 1260 for an event with no effect on ventricular pacing. In the absence 1262 of a premature signal, the left-ventricular cardiac pacemaker starts 1264 a left atrium to left ventricular (AV) escape interval that is representative of a typical time from an atrial beat to a left ventricular beat in sinus rhythm.

Terms "substantially", "essentially", or "approximately", that may be used herein, relate to an industry-accepted tolerance to the corresponding term. Such an industry-accepted tolerance ranges from less than one percent to twenty percent and corresponds to, but is not limited to, component values, integrated circuit process variations, temperature variations, rise and fall times, and/or thermal noise. The term "coupled", as may be used herein, includes direct coupling and indirect coupling via another component, element, circuit, or module where, for indirect coupling, the intervening component, element, circuit, or module does not modify the information of a signal but may adjust its current level, voltage level, and/or power level. Inferred coupling, for example where one element is coupled to another element by inference, includes direct and indirect coupling between two elements in the same manner as "coupled".

While the present disclosure describes various embodiments, these embodiments are to be understood as illustrative and do not limit the claim scope. Many variations, modifications, additions and improvements of the described embodiments are possible. For example, those having ordinary skill in the art will readily implement the steps necessary to provide the structures and methods disclosed herein, and will understand that the process parameters, materials, and dimensions are given by way of example only. The parameters, materials, and dimensions can be varied to achieve the desired structure as well as modifications, which are within the scope of the claims. Variations and modifications of the embodiments disclosed herein may also be made while remaining within the scope of the following claims. For example, although the description has some focus on the pacemaker, system, structures, and techniques can otherwise be applicable to other uses, for example multi-site pacing for prevention of tachycardias in the atria or ventricles. Phraseology and terminology employed herein are for the purpose of the description and should not be regarded as limiting. With respect to the description, optimum dimensional relationships for the component parts are to include variations in size, materials, shape, form, function and manner of operation, assembly and use that are deemed readily apparent and obvious to one of ordinary skill in the art and all equivalent relationships to those illustrated in the drawings and described in the specification are intended to be encompassed by the present description. Therefore, the foregoing is considered as illustrative only of the principles of structure and operation. Numerous modifications and changes will readily occur to those of ordinary skill in the art whereby the scope is not limited to the exact construction and operation shown and described, and accordingly, all suitable modifications and equivalents may be included.

What is claimed is:

1. A method of operating a cardiac pacing system comprising:
   using electrodes of a subcutaneous implantable cardioverter-defibrillator (SICD) to sense cardiac signals in one or more chambers of the patient's heart;
   using the electrodes of the SICD to send a triggering signal to a leadless pacemaker by conducted communication between the SICD and the leadless pacemaker;
   using a pair of electrodes of the leadless pacemaker to receive the triggering signal from the SICD;
   using the pair of electrodes of the leadless pacemaker, which were used to receive the triggering signal from the SICD, to perform pacing in a chamber of the patient's heart; and
   using the pair of electrodes of the leadless pacemaker, which were used to receive the triggering signal from the SICD and to perform the pacing, to convey information to the SICD via conducted communication by discharging a capacitor, coupled across the pair of electrodes of the leadless pacemaker, to form an electrical pulse during a refractory period of the heart and encoding the information to be conveyed on the electrical pulse.

2. The method of claim 1, further comprising:
   controlling charging of the capacitor coupled across the pair of electrodes of the leadless pacemaker, to control recharging of the capacitor;
   wherein the controlling charging includes discontinuing recharging when a power source terminal voltage falls below a predetermined value to ensure sufficient voltage for powering the leadless cardiac pacemaker.

3. The method of claim 1, further comprising ensuring that circuitry of the leadless pacemaker consumes no more than 64 microwatts.

4. The method of claim 1, further comprising ensuring that a primary power supply of the leadless pacemaker sources no more than 70 microwatts instantaneously.

5. The method of claim 1, further comprising:
   using the pair of electrodes of the leadless pacemaker to receive a signal having a pulse duration from the SICD; and
   the leadless pacemaker determining whether the signal is a triggering signal based on the pulse duration of the signal.

6. The method of claim 1, further comprising:
   the leadless pacemaker determining whether a triggering signal has arrived within a predetermined limit; and
   in response to the leadless pacemaker determining that the triggering signal has arrived within the predetermined limit, the leadless pacemaker activating delivery of a pacing pulse following a predetermined delay.

7. The method of claim 1, further comprising using the SICD to identify depolarization of the one or more chambers of the patient's heart by using the information conveyed to the SICD from the leadless pacemaker.

8. The method of claim 1, wherein the triggering signal sent by the SICD to the leadless pacemaker configures the leadless pacemaker to deliver overdrive anti-tachycardia pacing.

9. The method of claim 1, further comprising:
using a low-gain setting of a receiving amplifier of the leadless pacemaker to detect an edge of a pacing pulse;
switching the setting of the receiving amplifier to a high-gain setting to decode the triggering signal of the SICD.

10. The method of claim 1, further comprising using the SICD to detect an arrhythmia by using the information conveyed to the SICD by the leadless pacemaker.

11. The method of claim 10, further comprising using the triggering signals from the SICD to configure the leadless pacemaker to deliver anti-arrhythmia pacing.

12. The method of claim 10, further comprising using the triggering signals from the SICD to configure the leadless pacemaker and at least a second leadless pacemaker for multi-site pacing.

13. A method of operating a cardiac pacing system comprising:
using electrodes of a subcutaneous implantable cardioverter-defibrillator (SICD) to sense signals from one or more chambers of the patient's heart;
using the electrodes of the SICD to send a triggering signal to one or more leadless pacemakers by conducted communication between the SICD and the one or more leadless pacemakers;
using electrodes of the one or more leadless pacemakers to receive the triggering signal from the SICD;
using the electrodes of the one or more leadless pacemakers, which were used to receive the triggering signal from the SICD, to perform pacing in one or more chambers of the patient's heart; and
using the electrodes of the one or more leadless pacemakers, which were used to receive the triggering signal from the SICD and to perform the pacing, to convey information to the SICD via conducted communication by discharging a capacitor, coupled across at least one pair of the electrodes of the one or more leadless pacemakers, to form an electrical pulse during a refractory period of the heart and encoding the information to be conveyed on the electrical pulse.

14. The method of claim 13, wherein:
using the electrodes of the one or more leadless pacemakers to receive the triggering signal from the SICD comprises using the electrodes of three or more leadless pacemakers to receive the triggering signal from the SICD; and
using the electrodes of the one or more leadless pacemakers, which were used to receive the triggering signal from the SICD, to perform pacing in one or more chambers of the patient's heart comprises using the electrodes of at least three leadless pacemakers, which were used to receive the triggering signal from the SICD, to perform pacing in at least three chambers of the patient's heart for cardiac resynchronization therapy.

15. The method of claim 13, further comprising using the information conveyed to the SICD from the one or more leadless pacemakers to identify depolarization of the one or more chambers of the patient's heart.

16. The method of claim 13, wherein the triggering signal sent by the SICD to the one or more leadless pacemakers configures the one or more leadless pacemakers to deliver overdrive anti-tachycardia pacing.

17. The method of claim 13, further comprising:
using a low-gain setting of a receiving amplifier of the one or more leadless pacemakers to detect an edge of the triggering signal;
switching the setting of the receiving amplifier to a high-gain setting to decode the triggering signal.

18. The method of claim 13, further comprising using the SICD to detect an arrhythmia using the information conveyed to the SICD by the one or more leadless pacemakers.

19. The method of claim 18, further comprising using the triggering signals from the SICD to configure the one or more leadless pacemakers to deliver anti-arrhythmia pacing.

20. The method of claim 18, further comprising using the triggering signals from the SICD to configure at least two leadless pacemakers for multi-site pacing such as to provide synchronized depolarization for tachyarrhythmia prevention.

* * * * *